United States Patent
Isner et al.

(10) Patent No.: US 6,676,937 B1
(45) Date of Patent: Jan. 13, 2004

(54) COMPOSITIONS AND METHODS FOR MODULATING VASCULARIZATION

(75) Inventors: Jeffrey M. Isner, Weston, MA (US); Takayuki Asahara, Arlington, MA (US)

(73) Assignee: Caritas St. Elizabeth's Medical Center of Boston Inc., Boston, MA (US)

(*) Notice: Subject to any disclaimer, the term of this patent is extended or adjusted under 35 U.S.C. 154(b) by 0 days.

(21) Appl. No.: 09/265,041

(22) Filed: Mar. 9, 1999

Related U.S. Application Data

(60) Provisional application No. 60/077,262, filed on Mar. 9, 1998.

(51) Int. Cl.$^7$ ................. A01N 63/00; A61K 45/00; A61K 31/70; C12N 15/63; C12N 5/08

(52) U.S. Cl. .................. 424/93.7; 424/85.1; 514/44; 435/325; 435/355; 435/372; 435/455

(58) Field of Search .................. 424/93.7, 85.1, 424/85.2, 93.11, 93.71; 514/44; 435/325, 375, 355, 372, 455

(56) References Cited

U.S. PATENT DOCUMENTS

| | | | |
|---|---|---|---|
| 4,808,402 A | | 2/1989 | Leibovich et al. |
| 4,879,282 A | | 11/1989 | Saliba, Jr. |
| 5,229,496 A | | 7/1993 | Deeley et al. |
| 5,240,848 A | | 8/1993 | Keck et al. |
| 5,612,211 A | * | 3/1997 | Wilson et al. ............... 435/378 |
| 5,646,043 A | * | 7/1997 | Emerson et al. ............ 435/373 |
| 5,880,090 A | | 3/1999 | Hammond et al. |
| 5,941,868 A | * | 8/1999 | Kaplan et al. ............... 604/500 |
| 5,980,887 A | * | 11/1999 | Isner et al. ................. 424/93.7 |
| 6,121,246 A | * | 9/2000 | Isner ........................... 514/44 |
| 6,258,787 B1 | * | 7/2001 | Isner ........................... 514/44 |

FOREIGN PATENT DOCUMENTS

| | | |
|---|---|---|
| WO | 86/00639 | 1/1986 |
| WO | 96/39421 | 12/1996 |
| WO | 96/39515 | 12/1996 |

OTHER PUBLICATIONS

Eck, S.L. & wilson, J.M. Gene–based therapy. In Goodman & gilman's The Pharmacological basis of therapeutics. Ninth Edition, pp. 77–101, 1996.*
Verma, I.M. & Somia, N. Gene therapy–promises, problems and prospects. Nature 389: 239–242, 1997.*
Miller, N. & Vile, R. Targeted vectors for gene therapy. FASEB J. 9: 190–199, 1995.*
Deonarain, M.P. Ligand–targeted receptor–mediated vectors for gene delivery. Exp. Opin. Ther. Patents 8: 53–69, 1998.*
Shi et al., Evidence for circulating bone marrow–derived endothelial cells, 1998, BLOOD, vol. 92, pp. 362–367.*
Ngo et al., Computational complexity, protein structure prediction, and the levinthal paradox, 1994. In: The Folding Potein and Tertiary Structure Prediction, (Merz, K. et al., eds.), Birkhauser, Boston, pp. 491–495.*
Rudinger, Characteristics of the amino acids as components of a peptide hormone sequence, 1976. In: Peptide Hormones, (J.A. Parsons, Ed.), University Park Press, Baltimore pp. 1–7.*
Sunderkotter, C., et al., *Pharmac. Ther.* 51:195–216 (1991).
Takahashi, T., et al., *Nature Medicine* 5/4:434–438 (1999).
Bradbury, et al., *Nature* 298:686–688 (1982).
Aglietta, M. *J. Clin. Invest.*, 83: 551–557.
Andrews, et al., *Blood*, 67:842–845 (1986).
Asahara, *Science*, 275: 964–967 (1997).
Brugger et al., *N. Engl. J. Med.*, 333: 283–287 (1995).
Bussolini, et al., *J. Clin. Invest.*, 87: 986–995 (1991).
Cantrell, et al., *Proc. Natl. Acad. Sci.* 82: 6250–24 (1985).
Clark, et al., *Science*, 236: 1229–1237 (1987).
Dainiak, *Blood*, 78: 264–276 (1991).
Dedhar, et al., *Proc. Natl. Acad. Sci USA*, 85: 9253–9257 (1988).
Folkman, et al., *J. Biol. Chem.*, 267: 10931–10934 (1992).
Friedlander, et al., *Science*, 270: 1500–1502 (1995).
Gasson, *Blood*, 77: 1131–1145 (1991).
Gianni et al., *Lancet*, 2: 580–584 (1989).
Hynes, R.O. *Cell*, 48: 549–554 (1987).
Isner, et al., *Lancet*, 348: 370–374 (1996).
Ito, et al., *Lab. Invest.*, 72: 532–538 (1995).
Janssens, et al., *J. Biol. Chem*, 267: 14519–14522 (1992).
Kim, et al., *Blood*, 91: 100–110 (1998).
Lamas, et al., *Proc. Natl. Acad. Sci. USA*, 89: 6348–6352 (1992).
Liesveld, et al., *Leukemia*, 8: 2111–2117 (1994).
Millauer, et al., *Cell*, 72: 835–846 (1993).
Pardanaud, et al., *Development*, 105: 473–485 (1989).
Torok–Storb, *Blood*, 72: 373–385 (1988).
Risau, *FASEB J.*, 9: 926–933 (1995).
Sato, et al., *Nature*, 376: 70–74 (1995).
Senger, et al., *Am. J. Pathol.*, 149: 293–305 (1996).
Shalaby, et al., *Nature*, 376: 62–66 (1995).
Sieff, *J. Clin. Invest*, 79: 1549–1557 (1987).

(List continued on next page.)

*Primary Examiner*—David Guzo
*Assistant Examiner*—Quang Nguyen
(74) *Attorney, Agent, or Firm*—David G. Conlin; Robert L. Buchanan; Edwards & Angell, LLP

(57) ABSTRACT

The present invention generally provides methods for modulating formation of new blood vessels. In one embodiment, the methods include administering to a mammal an effective amount of granulocyte macrophage-colony stimulating factor (GM-CSF) sufficient to form the new blood vessels. Additionally provided are methods for preventing or reducing the severity of blood vessel damage in a mammal which methods preferably include administering to the mammal an effective amount of GM-CSF. Provided also as part of this invention are pharmaceutical products and kits for inducing formation of new blood vessels in the mammal.

24 Claims, 16 Drawing Sheets

OTHER PUBLICATIONS

Socinski, et al., *Lancet*, 1: 1194–1198 (1988).
Soldi, et al., *Blood*, 863–872 (1997).
Soligo, et al., *Leukemia*, 5: 1026–1030 (1991).
Takeshita et al., Lab. Invest. 75: 487–501 (1996).
Takeshita, et al., *J. Clin. Invest.*, 93: 662–670 (1994).
Tsurumi, et al., *Circulation*, 94: 3281–3290 (1996).
Tschudi, et al., *J. Clin. Invest.*, 98: 899–905 (1996).
Vecchi, et al., *Eur. J. Cell Biol.*, 63: 247–254 (1994).
Voyta, et al., *J. Cell. Biol.*, 99: 2034–2040 (1984).
Weyrich, et al., *Circ. Res.* 75: 692–700 (1994).
Yamaguchi, et al., *Development*, 118: 489–498 (1993).

* cited by examiner

Control GMCSF

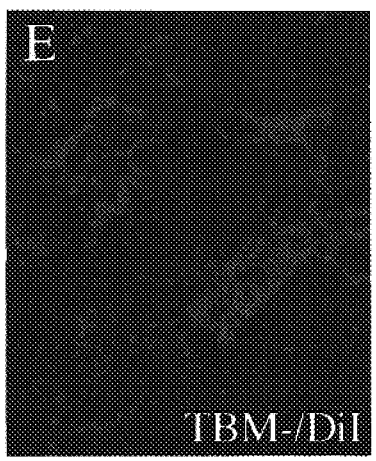
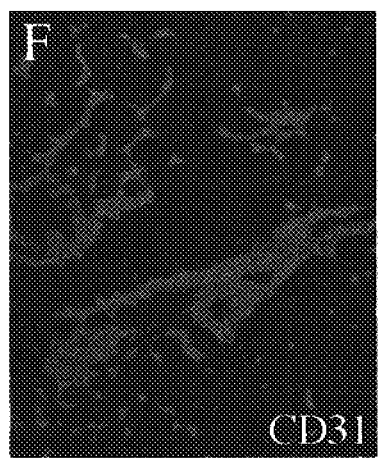
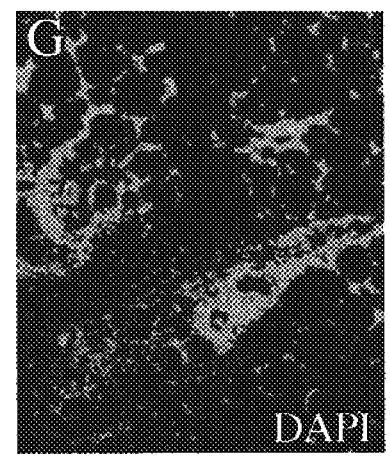
FIG. 4E  FIG. 4F  FIG. 4G
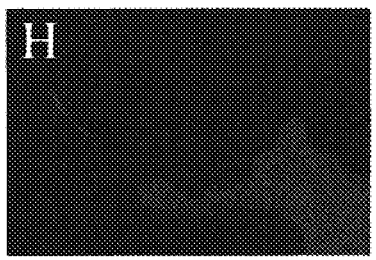
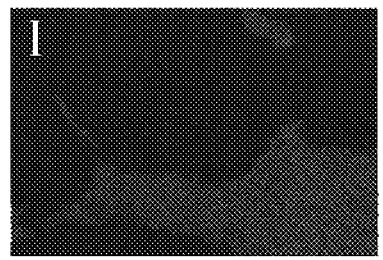
FIG. 4H  FIG. 4I  FIG. 4J

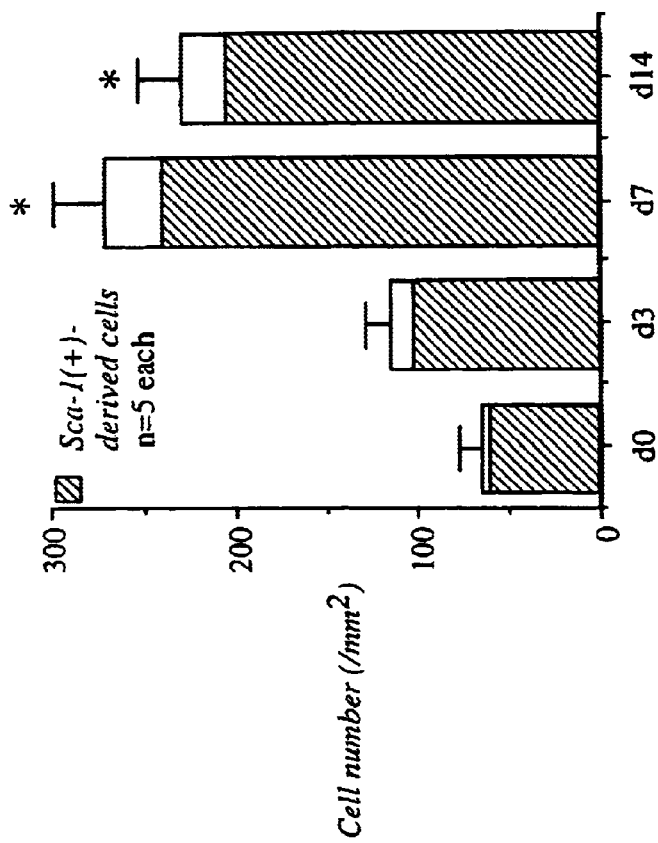
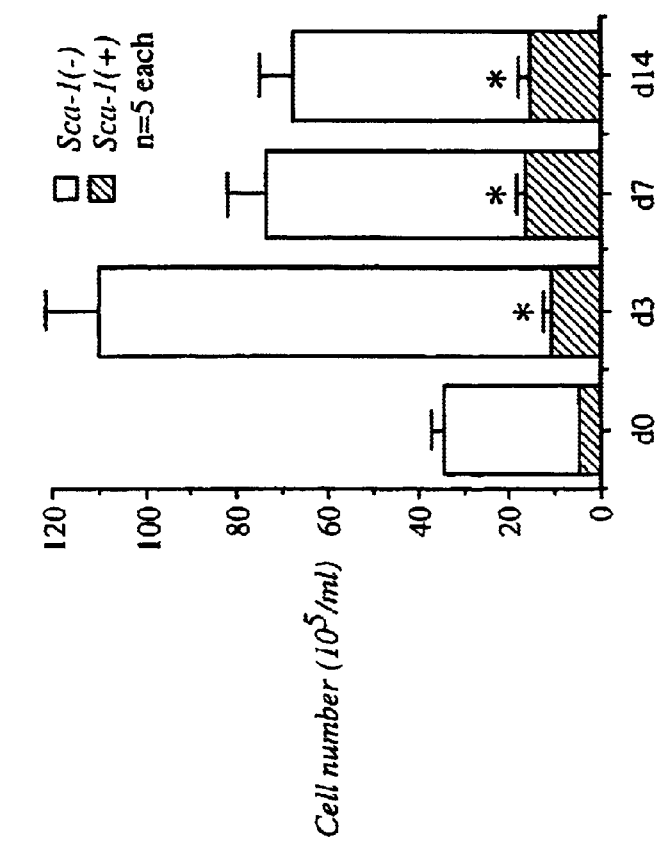
FIG. 5B
FIG. 5A

Sham   Ischemia

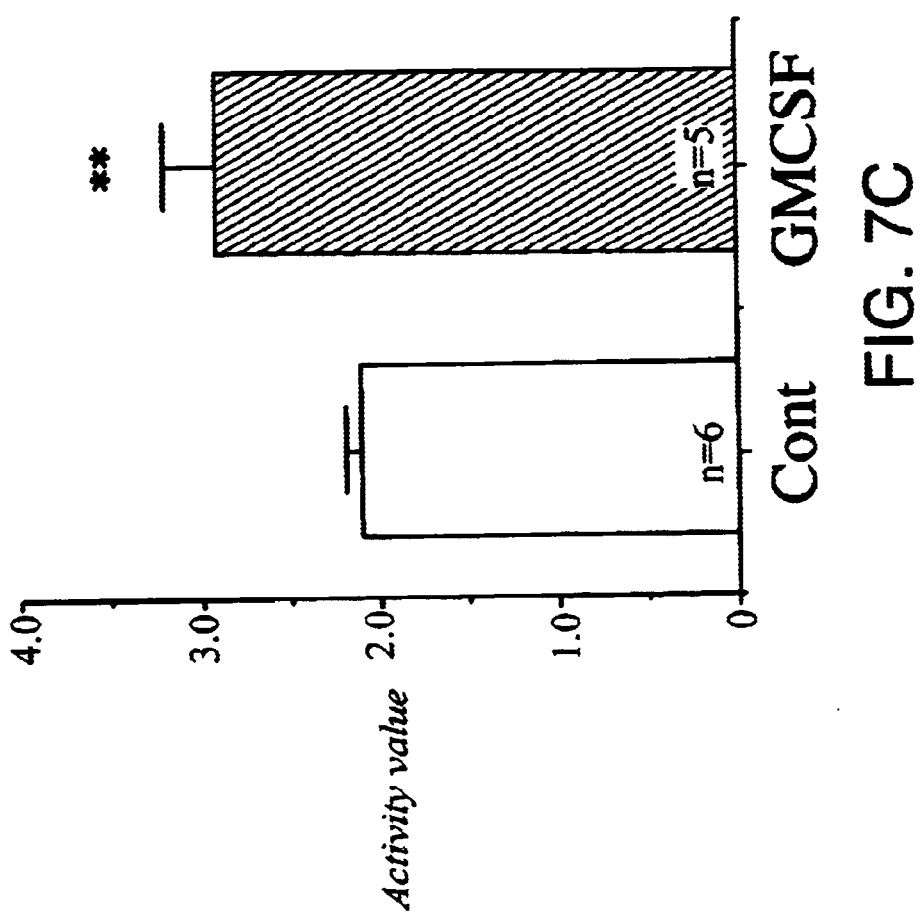

COMPOSITIONS AND METHODS FOR MODULATING VASCULARIZATION

CROSS REFERENCE TO RELATED APPLICATION

The present application is a continuation of U.S. Provisional Application No. 60/077,262, filed on Mar. 9, 1998; the disclosure of which is hereby incorporated by reference.

STATEMENT OF GOVERNMENT INTEREST

Funding for the present invention was provided in part by the Government of the United States by virtue of grants HL 40518, HL02824 and HL57516 by the National Institutes of Health. Accordingly, the Government of the United States has certain rights in and to the invention claimed herein.

FIELD OF THE INVENTION

The present invention relates to methods for modulating vascularization particularly in a mammal. In one aspect, methods are provided for modulating vascularization that includes administrating to the mammal an effective amount of granulocyte macrophage-colony stimulating factor (GM-CSF). Further provided are methods for treating or detecting damaged blood vessels in the mammal. The invention has a wide spectrum of useful applications including inducing formation of new blood vessels in the mammal.

BACKGROUND OF THE INVENTION

There is nearly universal recognition that blood vessels help supply oxygen and nutrients to living tissues. Blood vessels also facilitate removal of waste products. Blood vessels are renewed by a process termed "angiogenesis". See generally Folkman and Shing, J. Biol. Chem. 267 (16), 10931–10934 (1992).

Angiogenesis is understood to be important for the well-being of most mammals. As an illustration, angiogenesis has been disclosed as being an essential process for reproduction, development and wound repair.

There have been reports that inappropriate angiogenesis can have severe consequences. For example, it has been disclosed that solid tumor growth is facilitated by vascularization. There is broad support for the concept that mammals must regulate angiogenesis extensively.

There has been much attention directed to understanding how angiogeneis is controlled. In particular, angiogenesis is believed to begin with the degradation of the basement membrane by proteases secreted from endothelial cells (EC) activated by mitogens, e.g., vascular endothelial growth factor (ie. VEGF-1), basic fibroblast growth factor (bFGF) and/or others. The cells migrate and proliferate, leading to the formation of solid endothelial cell sprouts into the stromal space, then, vascular loops are formed and capillary tubes develop with formation of tight junctions and deposition of new basement membrane.

In adults, it has been disclosed that the proliferation rate of endothelial cells is typically low, compared to other cell types in the body. The turnover time of these cells can exceed one thousand days. Physiological exceptions in which angiogenesis results in rapid proliferation occurs under tight regulation are found in the female reproduction system and during wound healing. It has been reported that the rate of angiogenesis involves a change in the local equilibrium between positive and negative regulators of the growth of microvessels.

Abnormal angiogenesis is thought to occur when the body loses its control of angiogenesis, resulting in either excessive or insufficient blood vessel growth. For instance, conditions such as ulcers, strokes, and heart attacks may result from the absence of angiogenesis normally required for natural healing. In contrast, excessive blood vessel proliferation can facilitate tumor growth, blindness, psoriasis, rheumatoid arthritis, as well as other medical conditions.

The therapeutic implications of angiogenic growth factors were first described by Folkman and colleagues over two decades ago (Folkman, N. Engl. J. Med., 85:1182–1186 (1971)). Recent work has established the feasibility of using recombinant angiogenic growth factors, such as fibroblast growth factor (FGF) family (Yanagisawa-Miwa, et al., Science, 257:1401–1403 (1992) and Baffour, et al., J Vasc Surg, 16:181–91 (1992)), endothelial cell growth factor (ECGF)(Pu, et al., J Surg Res, 54:575–83 (1993)), and vascular endothelial growth factor (VEGF-1) to expedite and/or augment collateral artery development in animal models of myocardial and hindlimb ischemia (Takeshita, et al., Circulation, 90:228–234 (1994) and Takeshita, et al., J Clin Invest, 93:662–70 (1–994)).

The feasibility of using gene therapy to enhance angiogenesis has received recognition. For example, there have been reports that angiogenesis can facilitate treatment of ischemia in a rabbit model and in human clinical trials. Particular success has been achieved using VEGF-1 administered as a balloon gene delivery system. Successful transfer and sustained expression of the VEGF-1 gene in the vessel wall subsequently augmented neovascularization in the ischemic limb (Takeshita, et al., Laboratory Investigation, 75:487–502 (1996); Isner, et al., Lancet, 348:370 (1996)). In addition, it has been reported that direct intramuscular injection of DNA encoding VEGF-1 into ischemic tissue induces angiogenesis, providing the ischemic tissue with increased blood vessels (Tsurumi et al., Circulation, 94(12):3281–3290 (1996)).

Alternative methods for promoting angiogenesis are desirable for a number of reasons. For example, it is believed that native endothelial progenitor cell (EPC) number and/or viability decreases over time. Thus, in certain patient populations, e.g., the elderly, EPCs capable of responding to angiogenic proteins may be limited. Also, such patients may not respond well to conventional therapeutic approaches.

There have been reports that at least some of these problems can be reduced by administering isolated EPCs to patients and especially those undergoing treatment for ischemic disease. However, this suggestion is believed to be prohibitively expensive as it can require isolation and maintenance of patient cells. Moreover, handling of patient cells can pose a significant health risk to both the patient and attending personnel in some circumstances.

Granulocyte macrophage colony stimulating factor (GM-CSF) has been shown to exert a regulatory effect on granulocyte-committed progenitor cells to increase circulating granulocyte levels (Gasson, J. C., Blood 77:113 1 (1991). In particular, GM-CSF acts as a growth factor for granulocyte, monocyte and eosinophil progenitors.

Administration of GM-CSF to human and non-human primates results in increased numbers of circulating neutrophils, as well as eosinophils, monocytes and lymphocytes. Accordingly, GM-CSF is believed to be particularly useful in accelerating recovery from neutropenia in patients subjected to radiation or chemotherapy, or following bone marrow transplantation. In addition, although GM-CSF is less potent than other cytokines, e.g., FGF, in promoting EC proliferation, GM-CSF activates a fully migrating phenotype. (Bussolino, et al., J. Clin. Invent., 87:986 (1991).

Accordingly, it would be desirable to have methods for modulating vascularization in a mammal and especially a human patient. It would be particularly desirable to have methods that increase EPC mobilization and neovascularization (formation of new blood vessels) in the patient that do not require isolation of EPC cells.

SUMMARY OF THE INVENTION

The present invention generally relates to methods for modulating vascularization in a mammal. In one aspect, the invention provides methods for increasing vascularization that includes administrating to the mammal an effective amount of a vascularization modulating agent, such as granulocyte macrophage-colony stimulating factor (GM-CSF), VEGF, Steel factor (SLF, also known as Stem cell factor (SCF)), stromal cell-derived factor (SDF-1), granulocyte-colony stimulating factor (G-CSF), HGF, Angiopoietin-1, Angiopoietin-2, M-CSF, b-FGF, and FLT-3 ligand, and effective fragment thereof, or DNA coding for such vascularization modulating agents. Such materials have sometimes previously been described as "hematopoietic factors." and/or "hematopoietic proteins." Disclosure relating to these and other hematopoietic factors can be found in Kim, C. H. and Broxmeyer, H. E. (1998) *Blood*, 91:100; Turner, M. L. and Sweetenham, J. W., Br. J. *Haematol.* (1996) 94:592; Aiuuti, A. et al. (1997) *J. Exp. Med.* 185:111; Bleul, C. et al. (1996) *J. Exp. Med.* 184:1101; Sudo, Y. et al. (1 997) *Blood*, 89: 3166; as well as references disclosed therein. Prior to the present invention, it was not kown that GM-CSF or other hematopoietic factors could potentiate endothelial progenitor cells, or modulate neovascularization as described herein.

Alternatively, instead of the proteins themselves or effective fragments thereof, the DNA coding for the vascularization modulating agents can be administered to the site where neovascularization is desired, as further discussed below. The invention also relates to methods for treating or detecting damaged blood vessels in the mammal. The invention has many uses including preventing or reducing the severity of blood vessel damage associated with ischemia or related conditions.

We have now discovered that hematopoietic factors such as granulocyte-macrophage colony-stimulating factor (GM-CSF), modulate endothelial progenitor cell (EPC) mobilization and neovascularization (blood vessel formation). In particular, we have found that GM-CSF and other hematopoietic factors increase EPC mobilization and enhances neovascularization. This observation was surprising and unexpected in light of prior reports addressing GM-CSF activity in vitro and in vivo. Accordingly, this invention provides methods for using GM-CSF to promote EPC mobilization and to enhance neovascularization, especially in tissues in need of EPC mobilization and/or neovascularization.

In one aspect, the present invention provides a method for inducing neovascularization in a mammal. By the term "induction" is meant at least enhancing EPC mobilization and also preferably facilitating formation of new blood vessels in the mammal. EPC mobilization is understood to mean a significant increase in the frequency and differentiation of EPCs as determined by assays disclosed herein. In one embodiment, the method includes administering to the mammal an effective amount of a vascularization modulating factor such as granulocyte macrophage-colony stimulating factor (GM-CSF), that is preferably sufficient to induce the neovascularization in the mammal. Preferably, that amount of GM-CSF is also capable of modulating and particularly increasing frequency of EPCs in the mammal. A variety of methods for detecting and quantifying neovascularization, EPC frequency, the effectiveness of vascularization modulating agents, and other parameters of blood vessel growth are discussed below and in the examples.

In a particular embodiment of the method, the enhancement in EPC mobilization and particularly the increase in frequency of the EPCs is at least about 20% and preferably from between 50% to 500% as determined by a standard EPC isolation assay. That assay generally detects and quantifies EPC enrichment and is described in detail below.

In another particular embodiment of the method, the amount of administered modulating agent is sufficient to enhance EPC mobilization and especially to increase EPC differentiation in the mammal. Methods for detecting and quantifying EPC differentiation include those specific methods described below. Preferably, the increase in EPC differentiation is at least about 20%, preferably between from about 100% to 1000%, more preferably between from about 200% to 800% as determined by a standard EPC culture assay discussed below. More preferably, that amount of administered modulating agent is additionally sufficient to increase EPC differentiation by about the stated percent amounts following tissue ischemia as determined in a standard hindlimb ischemia assay as discussed below.

In another particular embodiment of the method, the amount of vascularization modulating agent administered to the mammal is sufficient to increase blood vessel size in the mammal. Methods for determining parameters of blood vessel size, e.g., length and circumference, are known in the field and are discussed below. Preferably, the amount of administered modulating agent is sufficient to increase blood vessel length by at least about 5%, more preferably between from about 10% to 50%, even more preferably about 20%, as determined by a standard blood vessel length assay discussed below. Preferably, the amount of modulating agent administered to the mammal is also sufficient to increase blood vessel circumference or diameter by the stated percent amounts as determined by a standard blood vessel diameter assay. As will be discussed below, it will often be preferred to detect and quantify changes in blood vessel size using a standard cornea micropocket assay, although other suitable assays can be used as needed.

In another particular embodiment of the method, the amount of administered vascularization modulating agent is sufficient to increase neovascularization by at least about 5%, preferably from between about 50% to 300%, and more preferably from between about 100% to 200% as determined by the standard cornea micropocket assay. Methods for performing that assay are known in the field and include those specific methods described below. Additionally, preferred amounts of GM-CSF are sufficient to improve ischemic hindlimb blood pressure by at least about 5%, preferably between from about 10% to 50% as determined by standard methods for measuring the blood pressure of desired vessels. More specific methods for measuring blood pressure particularly with new or damaged vessels include techniques optimized to quantify vessel pressure in the mouse hindlimb assay discussed below.

In another particular embodiment of the method, the amount of administered vascularization modulating agent is sufficient to increase EPC bone marrow (BM) derived EPC incorporation into foci by at least about 20% as determined by a standard murine BM transplantation model. Preferably, the increase is between from about 50% to 400%, more preferably between from about 100% to 300% as determined by that standard model. More specific methods for determining the increase in EPC incorporation into foci are found in the discussion and Examples which follow.

The methods of this invention are suitable for modulating and especially inducing neovascularization in a variety of animals including mammals. The term "mammal" is used herein to refer to a warm blooded animal such as a rodent, rabbit, or a primate and especially a human patient. Specific rodents and primates of interest include those animals representing accepted models of human disease including the mouse, rat, rabbit, and monkey. Particular human patients of interest include those which have, are suspected of having, or will include ischemic tissue. That ischemic tissue can arise by nearly any means including a surgical manipulation or a medical condition. Ischemic tissue is often associated with an ischemic vascular disease such as those specific conditions and diseases discussed below.

As will become more apparent from the discussion and Examples which follow, methods of this invention are highly compatible and can be used in combination with established or experimental methods for modulating neovascularization. In one embodiment, the invention includes methods for modulating and particularly inducing neovascularization in a mammal in which an effective amount of vascularization modulating agent is co-administered with an amount of at least one angiogenic protein. In many settings, it is believed that co-administration of the vascularization modulating agent and the angiogenic protein can positively impact neovascularization in the mammal, e.g., by providing additive or synergistic effects. A preferred angiogenic protein is a recognized endothelial cell mitogen such as those specific proteins discussed below. Methods for co-administering the vascularization modulating agent and the angiogenic protein are described below and will generally vary according to intended use.

The present invention also provides methods for preventing or reducing the severity of blood vessel damage in a mammal such as a human patient in need of such treatment. In one embodiment, the method includes administering to the mammal an effective amount of vascularization modulating agent such as GM-CSF. At about the same time or subsequent to that administration, the mammal is exposed to conditions conducive to damaging the blood vessels. Alternatively, administration of the vascularization modulating agent can occur after exposure to the conditions to reduce or block damage to the blood vessels. As discussed, many conditions are known to induce ischemic tissue in mammals which conditions can be particularly conducive to damaging blood vessels, e.g, invasive manipulations such as surgery, grafting, or angioplasty; infection or ischemia. Additional conditions and methods for administering the vascularization modulating agent are discussed below.

Preferred amounts of the vascularization modulating agent to use in the methods are sufficient to prevent or reduce the severity of the blood vessel damage in the mammal. Particular amounts of GM-CSF have already been mentioned above and include administration of an effective amount of GM-CSF sufficient to induce neovascularization in the mammal. Illustrative methods for quantifying an effective amount of vascularization modulating agents are discussed throughout this disclosure including the discussion and Examples which follow.

The present invention also provides methods for treating ischemic tissue and especially injured blood vessels in that tissue. Preferably, the method is conducted with a mammal and especially a human patient in need of such treatment. In one embodiment, the method includes as least one and preferably all of the following steps:

a) isolating endothelial progenitor cells (EPCs) from the mammal, b) contacting the isolated EPCs with an effective amount of at least one factor sufficient to induce proliferation of the EPCs; and c) administering the proliferated EPCs to the mammal in an amount sufficient to treat the injured blood vessel.

In a particular embodiment of the method, the factor is an angiogenic protein including those cytokines known to induce EPC proliferation especially in vitro. Illustrative factors and markers for detecting EPCs are discussed below. In one embodiment of the method, the blood vessel (or more than one blood vessel) can be injured by nearly any known means including trauma or an invasive manipulation such as implementation of balloon angioplasty or deployment of a stent or catheter. A particular stent is an endovascular stent. Alternatively, the vascular injury can be organic and derived from a pre-existing or on-going medical condition.

In another particular embodiment of the method, the vascularization modulating agent is administered to the mammal and especially the human patient alone or in combination (co-administered) with at least one angiogenic protein (or effective fragment thereof) such as those discussed below.

Additionally provided by this invention are methods for detecting presence of tissue damage in a mammal and especially a human patient. In one embodiment, the method includes contacting the mammal with a detectably-labeled population of EPCs; and detecting the detectably-labeled cells at or near the site of the tissue damage in the mammal. In this example, the EPCs can be harvested and optionally monitored or expanded in vitro by nearly any acceptable route including those specific methods discussed herein. The EPCs can be administered to the mammal by one or a combination of different approaches with intravenous injection being a preferred route for most applications. Methods for detectably-labeling cells are known in the field and include immunological or radioactive tagging as well as specific recombinant methods disclosed below.

In a particular embodiment of the method, the detectably-labeled EPCs can be used to "home-in" to a site of vascular damage, thereby providing a minimally invasive means of visualizing that site even when it is quite small. The detectably-labeled EPCs can be visualized by a variety of methods well-known in this field including those using tomography, magnetic resonance imaging, or related approaches.

In another embodiment of the method, the tissue damage is facilitated by ischemia, particularly an ischemic vascular disease such as those specifically mentioned below.

Also provided by this invention are methods for modulating the mobilization of EPCs which methods include administering to the mammal an effective amount of at least one hematopoietic factor. Preferred are methods that enhance EPC mobilization as determined by any suitable assay disclosed herein. For example, in a particular embodiment of the method, the enhancement in EPC mobilization and particulary the increase in frequency of the EPCs is at least about 20% and preferably from between 50% to 500% as determined by a standard EPC isolation assay.

In another particular embodiment of the method, the amount of administered hematopoietic factor is sufficient to enhance EPC mobilization and especially to increase EPC differentiation in the mammal. Methods for detecting and quantifying EPC differentiation include those specific methods described below. Preferably, the increase in EPC differentiation is at least about 20%, preferably between from about 100% to 1000%, more preferably between from about 200% to 800% as determined by a standard EPC culture assay discussed below. More preferably, that amount of administered hematopoietic factor is additionally sufficient to increase EPC differentiation by about the stated percent amounts following tissue ischemia as determined in a standard hindlimb ischemia assay as discussed below.

As discussed, it has been found that EPC mobilization facilitates significant induction of neovascularization in mammals. Thus, methods that modulate EPC mobilization and particularly enhance same can be used to induce neovascularization in the mammal and especially a human patient in need of such treatment. Methods of this invention which facilitate EPC mobilization including those employing at least one hematopoietic factor which use can be alone or in combination with other methods disclosed herein including those in which an effective amount of vascularization modulating agent is administered to the mammal alone or in combination (co-administered) with at least one angiogenic protein.

In particular, the invention provides methods for inducing neovascularization in a mammal and especially a human patient in need of such treatment which methods include administering to the mammal an effective amount of at least one vascularization modulating agent, preferably one vascularization modulating agent, which amount is sufficient to induce neovascularization in the mammal. That neovascularization can be detected and quantified if desired by the standard assays disclosed herein including the mouse cornea micropocket assay and blood vessel size assays. Preferred methods will enhance neovascularization in the mammal by the stated percent ranges discussed previously.

In one embodiment of the method, the effective amount of the vascularization modulating agent(s) is co-administered in combination with at least one angiogenic protein, preferably one angiogenic protein. The vascularization modulating agent can be administered to the mammal and especially a human patient in need of such treatment in conjunction with, subsequent to, or following administration of the angiogenic or other protein.

The invention also provides a pharmaceutical product that is preferably formulated to modulate and especially to induce neovascularization in a mammal. In a preferred embodiment, the product is provided sterile and optionally includes an effective amount of GM-CSF and optionally at least one angiogenic protein. In a particular embodiment, the product includes isolated endothelial progenitor cells (EPCs) in a formulation that is preferably physiologically acceptable to a mammal and particularly a human patient in need of the EPCs. Alternatively, the product can include a nucleic acid that encodes the GM-CSF and/or the angiogenic protein.

Also provided by this invention are kits preferably formulated for in vivo and particularly systemic introduction of isolated EPCs. In one embodiment, the kit includes isolated EPCs and optionally at least one angiogenic protein or nucleic acid encoding same. Preferred is a kit that optionally includes a pharmacologically acceptable carrier solution, nucleic acid or mitogen, means for delivering the EPCs and directions for using the kit. Acceptable means for delivering the EPCs are known in the field and include effective delivery by stent, catheter, syringe or related means.

Other aspects of the invention are disclosed infra.

BRIEF DESCRIPTION OF THE DRAWINGS

FIGS. 4A–4J are representations of photomicrographs showing that EPCs can home and incorporate into foci of neovascularization. (4A) cultured murine cells, (4B–D) homing of Sca-1$^+$ cells administered to the mouse, (4E–G) immunostaining of rabbit hindlimb muscle showing accumulation and colonization of EPCs, (4H–J) colonized TBM$^-$ cells establishing new vessels.

FIGS. 5A–B are graphs showing EPC kinetics in relation to development of hindlimb ischemia.

FIGS. 7A–C are graphs showing that detectably-labeled bone-marrow derived EPCs contribute to corneal neovascularization. (7A) corneal neovascularization in mice with hindlimb ischemia, (7B) rabbits pre-treated with GM-CSF, (7C) beta-galactosidase activity in GM-CSF control group.

DETAILED DESCRIPTION OF THE INVENTION

Figure 1A:
FIGS. 1A–D are representations of photomicrographs showing neovascularization following GM-CSF and VEGF-1 treatment in control (FIGS. 1A, 1C) and treated (FIGS. 1B and 1D) mice in a cornea micropocket assay.

As discussed, the present invention provides, in one aspect, methods for inducing neovascularization in a human patient that include administrating to the patient an effective amount of GM-CSF or an effective fragment thereof. As also discussed, that GM-CSF can be administered to the human patient alone or in combination (c-administered) with one or more of: at least one vascularization modulating agent, preferably one of such factors; at least one angiogenic protein, preferably one angiogenic protein; or an effective fragment thereof. Also provided are methods for enhancing EPC mobilization which methods include administration of an effective amount of at least one vascularization modulating agent, preferably one of such factors. Further provided are methods for treating or detecting damaged blood vessels in the human patient. The invention has a wide spectrum of uses including preventing or reducing the severity of blood vessel damage in the patient.

The invention particularly provides methods for inducing angiogenesis in ischemic tissue of a patient in need such treatment. In this embodiment, the methods generally include administering to the patient an effective amount of GM-CSF or other vascularization modulating agent disclosed herein. Administration of the GM-CSF (or co-adminstration with other another protein or proteins) can be as needed and may be implemented prior to, during or after formation of the ischemic tissue. Additionally, the GM-CSF can be administered as the sole active compound or it can be co-administered with at least one and preferably one angiogenic protein or other suitable protein or fragment as provided herein.

Administration of an effective amount GM-CSF or other vascularization modulating agent disclosed herein in accord with any of the methods disclosed herein can be implemented by one or a combination of different strategies including administering a DNA encoding same.

As discussed, methods of this invention have a wide spectrum of uses especially in a human patient, e.g., use in the prevention or treatment of at least one of trauma, graft rejection, cerebrovascular ischemia, renal ischemia, pulmonary ischemia, ischemia related to infection, limb ischemia, ischemic cardiomyopathy, cerebrovascular ischemia, and myocardial ischemia. Impacted tissue can be associated with nearly any physiological system in the patient including the circulatory system or the central nervous system, e.g., a limb, graft (e.g., muscle or nerve graft), or organ (e.g., heart, brain, kidney and lung). The ischemia may especially adversely impact heart or brain tissue as often occurs in cardiovascular disease or stroke, respectively.

In embodiments in which an effective amount of the vascularization modulating agent is administered to a mammal and especially a human patient to prevent or reduce the severity of a vascular condition and particularly ischemia, the vascularization modulating agent will preferably be administered at least about 12 hours, preferably between from about 24 hours to 1 week up to about 10 days prior to exposure to conditions conducive to damaging blood vessels. If desired, the method can further include administering the vascularization modulating agent to the mammal following exposure to the conditions conducive to damaging the blood vessels. As discussed, the vascularization modulating agent can be administered alone or in combination with at least one angiogenic protein preferably one of such proteins.

Related methods for preventing or reducing the severity of the vascular condition can be employed which methods include administering alone or in combination (co-administration) with the GM-CSF one or more of: at least one hematopoietic factor, preferably one of such factors; or at least one angiogenic protein, preferably one of such proteins. Preferred methods of administration are disclosed herein.

Vessel injury is known to be facilitated by one or a combination of different tissue insults. For example, vessel injury often results from tissue trauma, surgery, e.g., balloon angioplasty and use of related devices (e.g., directional atherectomy, rotational atherectomy, laser angioplasty, transluminal extraction, pulse spray thrombolysis); and deployment of an endovascular stent or a vascular graft.

Specific EPCs in accord with this invention will be preferably associated with cell markers that can be detected by conventional immunological or related strategies. Preferred are EPCs having at least one of the following markers: CD34$^+$, flk-1$^+$ or tie-2$^+$. Methods for detecting EPCs with these markers are discussed in the Examples below.

As discussed above and in the Examples following, we have discovered means to promote angiogenesis and reendothelialize denuded blood vessels in mammals. These methods involve the use of vascularization modulating agent to mobilize endothelial cell (EC) progenitors. In accordance with the present invention, GM-CSF and other vascularization modulating agents can be used in a method for enhancing angiogenesis in a selected patient having an ischemic tissue i.e., a tissue having a deficiency in blood as the result of an ischemic disease such as cerebrovascular ischemia, renal ischemia, pulmonary ischemia, limb ischemia, ischemic cardiomyopathy and myocardial ischemia.

Additionally, in another embodiment, the vascularization modulating agent, alone or in combination with at least one other factor disclosed herein can be used to induce reendothelialization of an injured blood vessel, and thus reduce restenosis by indirectly inhibiting smooth muscle cell proliferation.

In one preferred embodiment, the vascularization modulating agent, alone or in combination with at least one other factor disclosed herein can be used to prepare a patient for angiogenesis. Some patient populations, typically elderly patients, may have either a limited number of ECs or a limited number of functional ECs. Thus, if one desires to promote angiogenesis, for example, to stimulate vascularization by using a potent angiogenesis promotor such as VEGF-1, such vascularization can be limited by the lack of EPCs. However, by administering e.g., GM-CSF at a time before administration of the angiogenesis promoter sufficient to allow mobilization of the ECs, one can potentiate the vascularization in those patients. Preferably, GM-CSF is administered about one week prior to treatment with the angiogenesis promoter.

The term "GM-CSF" as used herein shall be understood to refer to a natural or recombinantly prepared protein having substantial identity to an amino acid sequence of human GM-CSF as disclosed, for example, in published international application WO 86/00639, which is incorporated herein by reference. Recombinant human GM-CSF is hereinafter also referred to as "hGM-CSF."

Human GM-CSF (hGM-CSF) has been isolated and cloned, see published International Application No. PCT/EP 85/00326, filed Jul. 4, 1985 (published as WO 86/00639).

E. coli derived, non-glycosylated rhGM-CSF can be obtained by the methods described in publication of the International Application No. PCT/EP 85/00326, wherein two native GM-CSFs differing in a single amino acid are described.

The natural GM-CSF proteins used in the invention may be modified by changing the amino acid sequence thereof. For example, from 1 to 5 amino acids in their sequences may be changed, or their sequences may be lengthened, without changing the fundamental character thereof and provide modified proteins which are the full functional equivalents of the native proteins. Such functional equivalents may also be used in practicing the present invention. A GM-CSF differing by a single amino acid from the common native sequence is disclosed in U.S. Pat. No. 5,229,496 and has been produced in glycosylated form in yeast, and has been clinically demonstrated to be a biological equivalent of native GM-CSF, such modified form known as GM-CSF (Leu-23).

GM-CSF is commercially and clinically available as an analog polypeptide (Leu$^{23}$) under the trademark LEUKINE® (Immunex Corporation). The generic name for recombinant human Leu$^{23}$ GM-CSF analog protein expressed in yeast is Sargramostim. Cloning and expression of native sequence human GM-CSF was described in Cantrell et al., Proc Natl. Acad. Sci. U.S.A. 82:6250(1985).

The natural or recombinantly prepared proteins, and their functional equivalents used in the method of the invention are preferably purified and substantially cell-free, which may be accomplished by known procedures.

Additional protein and nucleic sequences relating to the factors disclosed herein including GM-CSF can be obtained through the National Center for Biotechnology Information ((NCBI)-Genetic Sequence Data Bank (Genbank). In particular, sequence listings can be obtained from Genbank at the National Library of Medicine, 38A, 8N05, Rockville Pike, Bethesda, Md. 20894. Genbank is also available on the internet. See generally Benson, D. A. et al. (1997) *Nucl. Acids. Res.* 25: 1 for a description of Genbank. Protein and nucleic sequences not specifically referenced can be found in Genbank or other sources disclosed herein.

In accord with the methods of this invention, GM-CSF can be administered to a mammal and particularly a human patient in need of such treatment. As an illustration, GM-CSF as well as therapeutic compositions including same are preferably administered parenterally. More specific examples of parenteral administration include subcutaneous, intravenous, intraarterial, intramuscular, and intraperitoneal, with subcutaneous being preferred.

In embodiments of this invention in which parenteral administration is selected, the GM-CSF will generally be formulated in a unit dosage injectable form (solution, suspension, emulsion), preferably in a pharmaceutically acceptable carrier medium that is inherently non-toxic and non-therapeutic. Examples of such vehicles include without limitation saline, Ringer's solution, dextrose solution, mannitol and normal serum albumin. Neutral buffered saline or saline mixed with serum albumin are exemplary appropriate vehicles. Non-aqueous vehicles such as fixed oils and ethyl oleate may also be used. Additional additives include substances to enhance isotonicity and chemical stability, e.g., buffers, preservatives and surfactants, such as Polysorbate 80. The preparation of parenterally acceptable protein solutions of proper pH, isotonicity, stability, etc., is within the skill of the art.

Preferably, the product is formulated by known procedures as a lyophilizate using appropriate excipient solutions (e.g., sucrose) as a diluent.

Preferred in vivo dosages the vascularization modulating agents are from about 1 μg/kg/day to about 100 μg/kg/day. Use of more specific dosages will be guided by parameters well-known to those in this field such as the specific condition to be treated and the general health of the subject. See also U.S. Pat. No. 5,578,301 for additional methods of administering GM-CSF. Preferred in vivo dosages for the hematopoietic proteins and angiogenic proteins disclosed herein will be within the same or similar range as for GM-CSF.

As discussed, for some applications it will be useful to augment the vascularization modulating agent administration by co-administering one or more of: at least one hematopoietic protein, at least one angiogenic protein; or an effective fragment thereof. This approach may be especially desirable where an increase (boost) in angiogenesis is needed. For example, in one embodiment, at least one angiogenic protein and preferably one of same will be administered to the patient in conjunction with, subsequent to, or prior to the administration of the GM-CSF. The angiogenic protein can be administered directly, e.g., intra-arterially, intramuscularly, or intravenously, or nucleic acid encoding the mitogen may be used. See, Baffour, et al., supra (bFGF); Pu, et al, *Circulation*, 88:208–215 (1993) (aFGF); Yanagisawa-Miwa, et al., supra (bFGF); Ferrara, et al., *Biochem. Biophys. Res. Commun.*, 161:851–855 (1989) (VEGF-1); (Takeshita, et al., *Circulation*, 90:228–234 (1994); Takeshita, et al., *Laboratory*, 75:487–502 (1996); Tsusumi, et al., *Circulation*, 94 (12):3281–3290 (1996)).

As another illustration, at least one hematopoietic protein and preferably one of such proteins can be administered to the human patient in need of such treatment in conjunction with, subsequent to, or prior to the administration of the GM-CSF. As discussed, at least one angiogenic protein can also be co-administered with the GM-CSF and hematopoietic protein. Methods for administering the hematopoietic protein will generally follow those discussed for administering the GM-CSF although other modes of administration may be suitable for some purposes.

It will be understood that the term "co-administration" is meant to describe preferred administration of at least two proteins disclosed herein to the mammal, ie., administration of one protein in conjunction with, subsequent to, or prior to administration of the other protein.

In embodiments in which co-administration of a DNA encoding and angiogenic or hematopoietic protein is desired, the nucleic acid encoding same can be administered to a blood vessel perfusing the ischemic tissue via a catheter, for example, a hydrogel catheter, as described by U.S. Pat. No. 5,652,225, the disclosure of which is herein incorporated by reference. The nucleic acid also can be delivered by injection directly into the ischemic tissue using the method described in PCT WO 97/14307.

As used herein the term "angiogenic protein" or related term such as "angiogenesis protein" means any protein, polypeptide, mutein or portion that is capable of, directly or indirectly, inducing blood vessel growth. Such proteins include, for example, acidic and basic fibroblast growth factors (aFGF and bFGF), vascular endothelial growth factor (VEGF-1), VEGF165, epidermal growth factor (EGF), transforming growth factor α and β (TGF-α and TFG-β), platelet-derived endothelial growth factor (PD-ECGF), platelet-derived growth factor (PDGF), tumor necrosis factor α (TNF-α), hepatocyte growth factor (HGF), insulin like growth factor (IGF), erythropoietin, colony stimulating factor (CSF), macrophage-CSF (M-CSF), granulocyte/macrophage CSF (GM-CSF), angiopoetin-1 (Ang1) and nitric oxidesynthase (NOS). See, Klagsbrun, et al., *Annu. Rev. Physiol.*, 53:217–239 (1991); Folkman, et al., *J. Biol. Chem.*, 267:10931–10934 (1992) and Symes, et al., *Current Opinion in Lipidology*, 5:305–312 (1994). Muteins or fragments of a mitogen may be used as long as they induce or promote blood vessel growth.

Preferred angiogenic proteins include vascular endothelial growth factors. One of the first of these was termed VEGF, now called VEGF-1, exists in several different isoforms that are produced by alternative splicing from a single gene containing eight exons (Tischer, et al., *J. Biol. Chem.*, 806, 11947–11954 (1991), Ferrara, *Trends Cardio. Med.*, 3, 244–250 (1993), Polterak, et al., *J. Biol. Chem.*, 272, 7151–7158 (1997)). Human VEGF isoforms consists of monomers of 121 (U.S. Pat. No. 5,219,739), 145, 165 (U.S. Pat. No. 5,332,671), 189 (U.S. Pat. No. 5,240,848) and 206 amino acids, each capable of making an active homodimer (Houck, et al., *Mol. Endocrinol.*, 8, 1806–1814 (1991)).

Other vascular endothelial growth factors include VEGF-B and VEGF-C (Joukou, et al., *J. of Cell. Phys.* 173:211–215 (1997), VEGF-2 (WO 96/39515), and VEGF-3 (WO 96/39421).

Preferably, the angiogenic protein contains a secretory signal sequence that facilitates secretion of the protein.

Proteins having native signal sequences, e.g., VEGF-1, are preferred. Proteins that do not have native signal sequences, e.g., bFGF, can be modified to contain such sequences using routine genetic manipulation techniques. See, Nabel et al., *Nature*, 362:844 (1993).

Reference herein to a "vascularization modulating agent", "hematopoietic factor" or related term, e.g., "hematopoietic protein" is used herein to denote recognized factors that increase mobilization of hematopoietic progenitor cells (HPC). Preferred hematopoietic factors include granulocyte-macrophage colony-stimulating factor (GM-CSF), VEGF, Steel factor (SLF, also known as Stem cell factor (SCF)), stromal cell-derived factor (SDF-1), granulocyte-colony stimulating factor (G-CSF), HGF, Angiopoietin-1, Angiopoietin-2, M-CSF, b-FGF, and FLT-3 ligand. Disclosure relating to these and other hematopoietic factors can be found in Kim, C. H. and Broxmeyer, H. E. (1998) *Blood*, 91: 100; Turner, M. L. and Sweetenham, J. W., *Br. J. Haematol.* (1996) 94: 592; Aiuuti, A. et al. (1997) *J. Exp. Med.* 185: 111; Bleul, C. et al. (1996) J Exp. Med. 184: 1101; Sudo, Y. et al. (1997) Blood, 89: 3166; as well as references disclosed therein.

The nucleotide sequence of numerous angiogenic proteins, are readily available through a number of computer databases, for example, GenBank, EMBL and Swiss-Prot. Using this information, a DNA segment encoding the desired may be chemically synthesized or, alternatively, such a DNA segment may be obtained using routine procedures in the art, e.g, PCR amplification.

In certain situations, it may be desirable to use nucleic acids encoding two or more different proteins in order optimize therapeutic outcome. For example, DNA encoding two proteins, e.g., VEGF-1 and bFGF, can be used, and provides an improvement over the use of bFGF alone. Or an angiogenic factor can be combined with other genes or their encoded gene products to enhance the activity of targeted cells, while simultaneously inducing angiogenesis, including, for example, nitric oxide synthase, L-arginine, fibronectin, urokinase, plasminogen activator and heparin.

The term "effective amount" means a sufficient amount of a compound, e.g. protein or nucleic acid delivered to produce an adequate level of the subject protein (e.g., GM-CSF, vascularization modulating agent, hematopoietic protein, angiogenic protein) i.e., levels capable of inducing endothelial cell growth and/or inducing angiogenesis as determined by standard assays disclosed throughout this application. Thus, the important aspect is the level of protein expressed. Accordingly, one can use multiple transcripts or one can have the gene under the control of a promoter that will result in high levels of expression. In an alternative embodiment, the gene would be under the control of a factor that results in extremely high levels of expression, e.g., tat and the corresponding tar element.

To simplify the manipulation and handling of the nucleic acid encoding the protein, the nucleic acid is preferably inserted into a cassette where it is operably linked to a promoter. The promoter must be capable of driving expression of the protein in cells of the desired target tissue. The selection of appropriate promoters can readily be accomplished. Preferably, one would use a high expression promoter. An example of a suitable promoter is the 763-base-pair cytomegalovirus (CMV) promoter. The Rous sarcoma virus (RSV) (Davis, et al., *Hum Gene Ther* 4:151 (1993)) and MMT promoters may also be used. Certain proteins can be expressed using their native promoter. Other elements that can enhance expression can also be included such as an enhancer or a system that results in high levels of expression such as a tat gene and tar element. This cassette can then be inserted into a vector, e.g., a plasmid vector such as pUC118, pBR322, or other known plasmid vectors, that includes, for example, an *E. coli* origin of replication. See, Sambrook, et al., *Molecular Cloning: A Laboratory Manual*, Cold Spring Harbor Laboratory press, (1989).

The plasmid vector may also include a selectable marker such as the β-lactamase gene for ampicillin resistance, provided that the marker polypeptide does not adversely effect the metabolism of the organism being treated. The cassette can also be bound to a nucleic acid binding moiety in a synthetic delivery system, such as the system disclosed in WO 95/22618.

Particular methods of the present invention may be used to treat blood vessel injuries that result in denuding of the endothelial lining of the vessel wall. For example, primary angioplasty is becoming widely used for the treatment of acute myocardial infarction. In addition, endovascular stents are becoming widely used as an adjunct to balloon angioplasty. Stents are useful for rescuing a sub-optimal primary result as well as for diminishing restenosis. To date, however, the liability of the endovascular prosthesis has been its susceptibility to thrombotic occlusion in approximately 3% of patients with arteries 3.3 mm or larger. If patients undergo stent deployment in arteries smaller than this the incidence of sub-acute thrombosis is even higher. Sub-acute thrombosis is currently prevented only by the aggressive use of anticoagulation. The combination of vascular intervention and intense anticoagulation creates significant risks with regard to peripheral vascular trauma at the time of the stent/angioplasty procedure. Acceleration of reendothelialization by administration of GM-CSF alone or in combination with other factors disclosed herein to a patient prior to undergoing angioplasty and/or stent deployment can stabilize an unstable plaque and prevent reocclusion. In this example, GM-CSF is preferably administered about 1 week prior to the denuding of the vessel wall.

The methods of the present invention may be used in conjunction a DNA encoding an endothelial cell mitogen in accordance with the method for the treatment of vascular injury disclosed in PCT/US96/15813.

As used herein the term "endothelial cell mitogen" means any protein, polypeptide, mutein or portion that is capable of inducing endothelial cell growth. Such proteins include, for example, vascular endothelial growth factor (VEGF-1), acidic fibroblast growth factor (aFGF), basic fibroblast growth factor (bFGF), hepatocyte growth factor (scatter factor), and colony stimulating factor (CSF). VEGF-1 is preferred.

In addition, the methods of the present invention may be used to accelerate the healing of graft tissue, e.g., vascular grafts, by potentiating vascularization.

Reference herein to a "standard EPC isolation assay" or other similar phrase means an assay that includes at least one of and preferably all of the following steps:

a) obtaining a peripheral blood sample from a subject mammal, preferably a rodent and especially a mouse, b) separating from the blood sample light-density mononuclear cells, c) contacting the separated mononuclear cells with beads that include a sequence capable of specifically binding Sca-1$^+$ cells and separating same from the mononuclear cells; and d) quantitating the Sca-1$^+$ cells, eg., by counting those cells manually.

See the following discussion and Examples for more specific disclosure relating to the standard EPC isolation assay.

By the term "standard EPC culture assay" or related term is meant an assay that includes at least one of and preferably all of the following steps.
  a) isolating Sca-1+ and Sca-1− cells from the peripheral blood of mouse, or TBM+ and TBM− cells from the peripheral blood of a rabbit, and detectably-labelling the cells (Sca-1+ and TBM−), e.g., with Di-I as provided herein,
  b) culturing the cells in a suitable dish or plate in medium for several days and usually for about 4 days,
  c) counting any attached spreading cells in the dish or plate as being Di-I labeled Sca-1+ or TBM− or non-labeled Sca-1− or TBM+,
  d) and quantitating specific positive cells as being indicative of EPCs.

More specific disclosure relating to the standard EPC culture assay can be found in the discussion and Examples that follow.

Reference herein to a "standard hind limb ischemia assay" or related term is meant to denote a conventional assay for inducing hindlimb ishemica in accepted animal models and particularly the mouse or rabbit. Disclosure relating to conducting the assay can be found in the Examples and Materials and Methods section that follows. See also Couffinhal, T. et al. (1998) *Am. J. Pathol., infra*; and Takeshita, S. et al. (1994) *J. Clinical. Invest.* 93: 662 for more disclosure relating to performing the assay.

Reference herein to a "standard blood vessel length assay" or "standard blood vessel diameter assay" generally means exposing a blood vessel of interest in the subject mammal (e.g., mouse or rabbit) and measuring the length or diameter of that vessel by conventional means following inspection of that vessel. Illustrative blood vessels such as certain arteries or veins which can be measured are provided below.

The phrase "standard cornea micropocket assay" or related term is used herein in particular reference to a mouse corneal neovascularization assay. The assay generally involves one and preferably all of the following steps.
  a) creating a corneal micropocket in at least one eye of a mouse,
  b) adding to the pocket a pellet including an acceptable polymer and at least one angiogenic protein, preferably VEGF-1,
  c) examining the mouse eye, e.g, by slit-lamp biomicroscopy for vascularization, typically a few days, e.g., 5 to 6 days following step b),
  d) marking EC cells in the eye, e.g., with BS-1 lectin; and
  e) quantitating vascularization and optionally EC cell counts in the eye.

For more specific disclosure relating to the standard cornea 2 5 micropocket assay, see the discussion and Examples which follow. If desired, the assay can include a control as a reference which control will include performing steps a)–e) above, except that step b) will include adding a pellet without the angiogenic protein.

Reference herein to a "standard murine bone marrow (BM) transplantation model" or similar phrase is meant at least one and preferably all of the following steps.
  a) obtaining detectably-labeled BM cells from a donor mammal and typically a mouse,
  b) isolating low-density BM mononuclear cells from the mouse,
  c) removing BM cells from a suitable recipient mouse, e.g, by irradiation,
  d) administering the isolated and detectably-labeled BM cells to the recipient mouse,
  e) exposing the recipient mouse to conditions conditions conducive to damaging blood vessels in the mouse, e.g., hindlimb ischemia,
  f) administering an effective amount of GM-CSF to the recipient mouse,
  g) harvesting at least one cornea from the recipient mouse; and
  h) detecting and quantitating any labeled BM cells in the cornea.

An illustrative detectable-label is beta-galactosidase enzyme activity. More specific information relating to the assay can be found in the discussion and Examples which follow.

Reference herein to an "effective fragment" of vascularization modulating agents such as GM-CSF, a hemopoietic protein, or angiogenic protein means an amino acid sequence that exhibits at least 70%, preferably between from about 75% to 95% of the vessel promoting activity of the corresponding full-length protein as determined by at least one standard assay as disclosed herein. Preferred are those assays which detect and preferably quantify EPC mobilization although other standard assays can be used. As an illustration, a preferred effective fragment of GM-CSF will have at least 70% and preferably from about 75% to 95% of the vessel promoting activity of full-length human GM-CSF (see the published International Application No. PCT/EP/85/00376 (W086/00639)) as determined in the standard corneal micropocket assay and especially the standard blood vessel length or diameter assays.

All documents mentioned herein are incorporated by reference herein in their entirety.

The present invention is further illustrated by the following examples. These examples are provided to aid in the understanding of the invention and are not construed as a limitation thereof

EXAMPLE 1

Modulation of EPC Kinetics by Cytokine Adminstration

Circulating EPCs may constitute a reparative response to injury. The hypothesis that cytokine-administration may mobilize EPCs and thereby augment therapeutic neovascularization was investigated as follows.

Figure 1B:
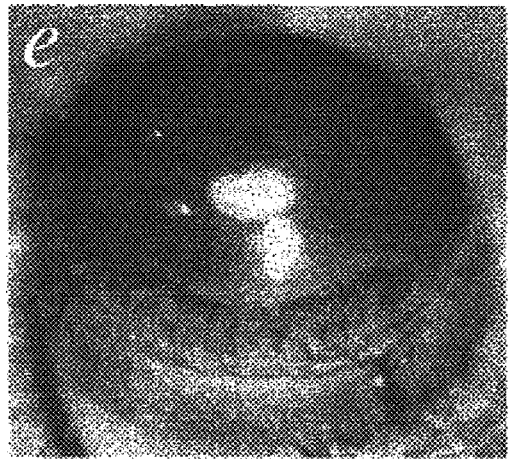
Figure 1C:
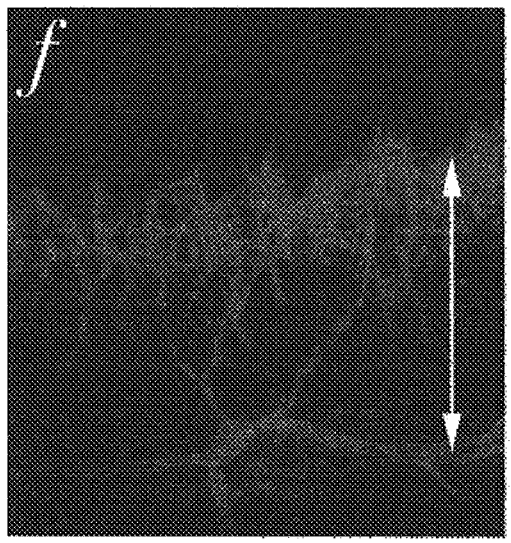
Figure 1D:
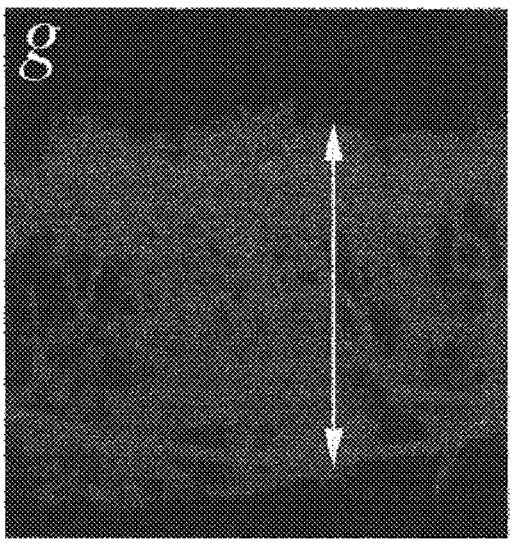
Figure 2A:
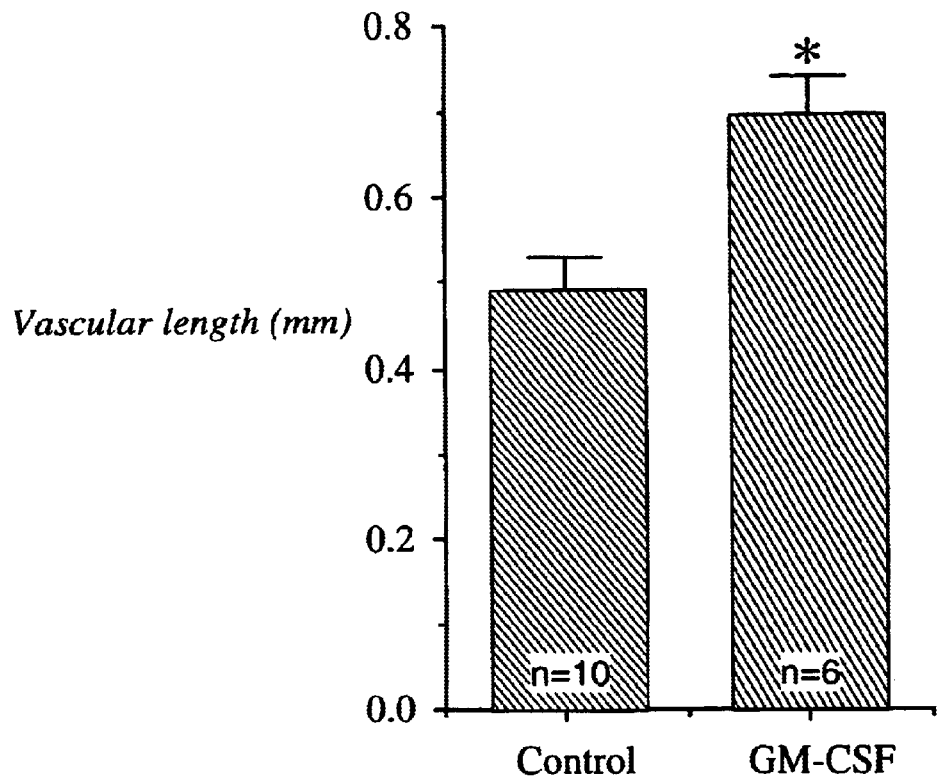
FIGS. 2A–B are graphs showing quantitation of increases in vessel length (2A) and vessel angle (2B) observed in the cornea micropocket assay.
Figure 2B:
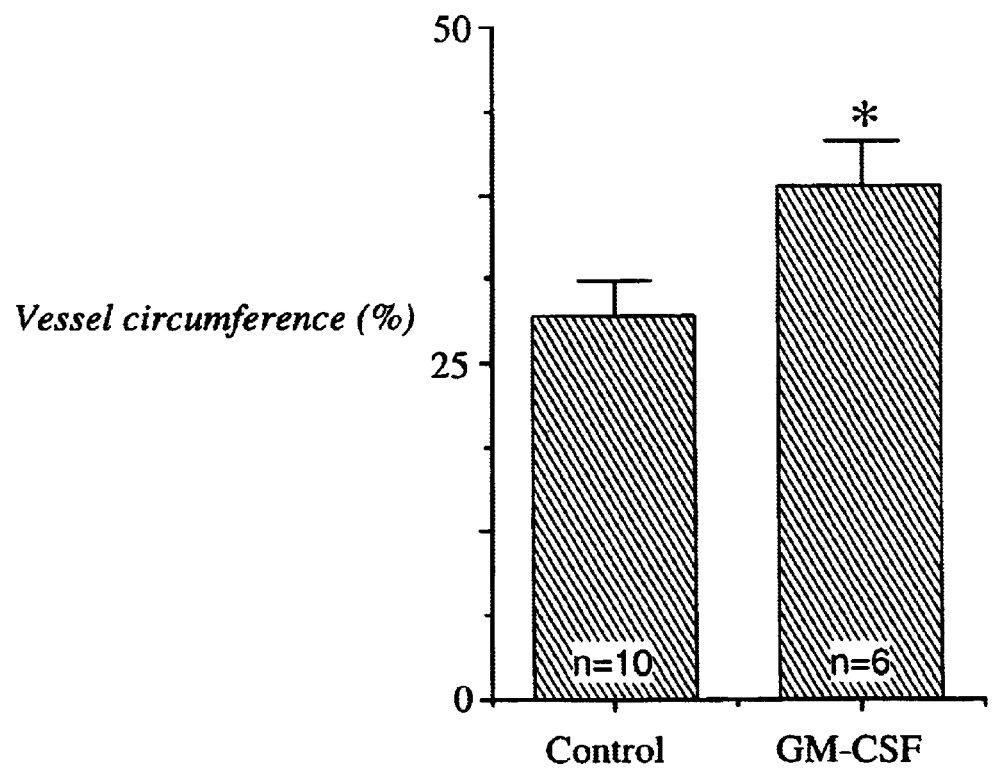

GM-CSF, which induces proliferation and differentiation of hematopoietic prognitor cells (Socinski, et al., *Lancet*, 1988;1: 1194–1198, Gianni, et al., *Lancet*, 1989;2:580–584) and cells of myeloid lineage (Clark, et al., Science 1987;236:1229–1237, Sieff, C., *J. Clin. Invest.* 1987;79:15491557), as well as non-hematopoietic cells including BM stroma cells (Dedhar, et al., *Proc. Natl. Acad. Sci USA* 1988;85:9253–9257) and ECs (Bussolini, et al., *J. Clin. Invest.*, 1991;87:986–995), was used to promote cytokine-induced EPC mobilization. To avoid a direct mitogenic effect on ECs, GM-CSF was administered for 7 days prior to creating the stimulus for neovascularization. De novo vascular formation was initially examined in the mouse cornea pocket assay described above. GM-GSF-pretreatment (intraperitoneal [i.p.] rmGM-CSF [R&D Systems] 500 ng/day) increased circulating EPCs (221% of untreated controls) at day 0, i.e., prior to creation of the cornea micropocket and insertion of VEGF pellet;

correspondingly, neovascularization at day 6 (FIGS. 1A–C) was augmented in comparison to control mice (length= 0.67±0.04 vs 0.53±0.04, p<0.05; angle (circumferential degrees occupied by neovascularity)=155±13 vs 117±12, p.<0.05) (FIGS. 1B–1D). See also FIGS. 2A and 2B.

EXAMPLE 2

Figure 3A:
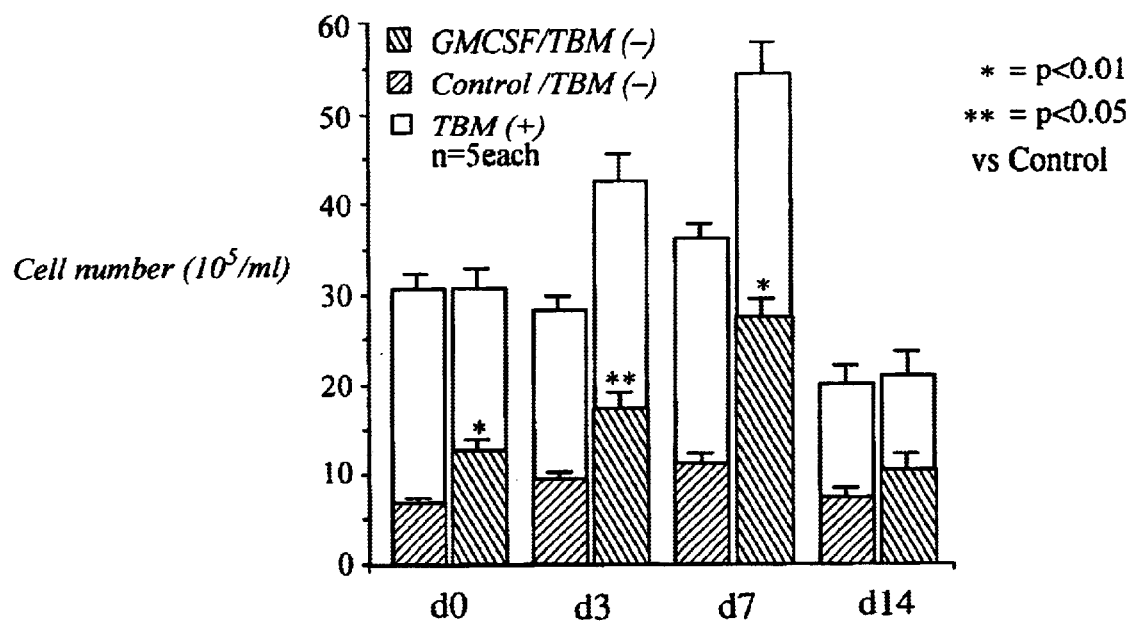
FIGS. 3A–C are graphs showing EPC frequency (3A), EPC differentiation (3B), blood pressure and capillary density (3C) following GM-CSF treatment in the rabbit hindlimb ischemia assay.
Figure 3B:
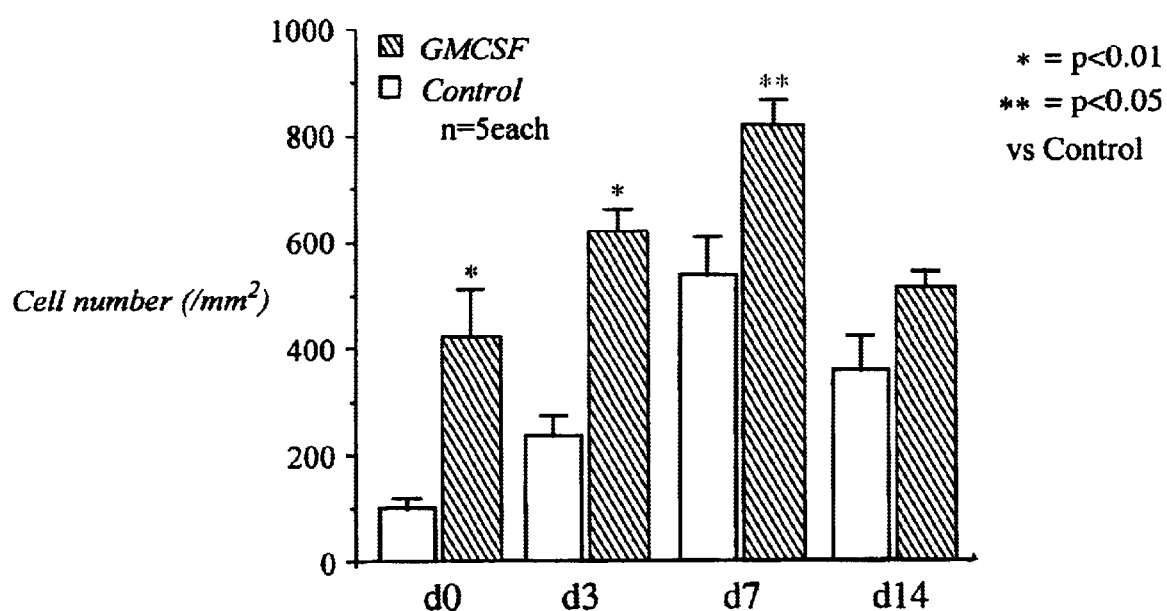
Figure 3C:
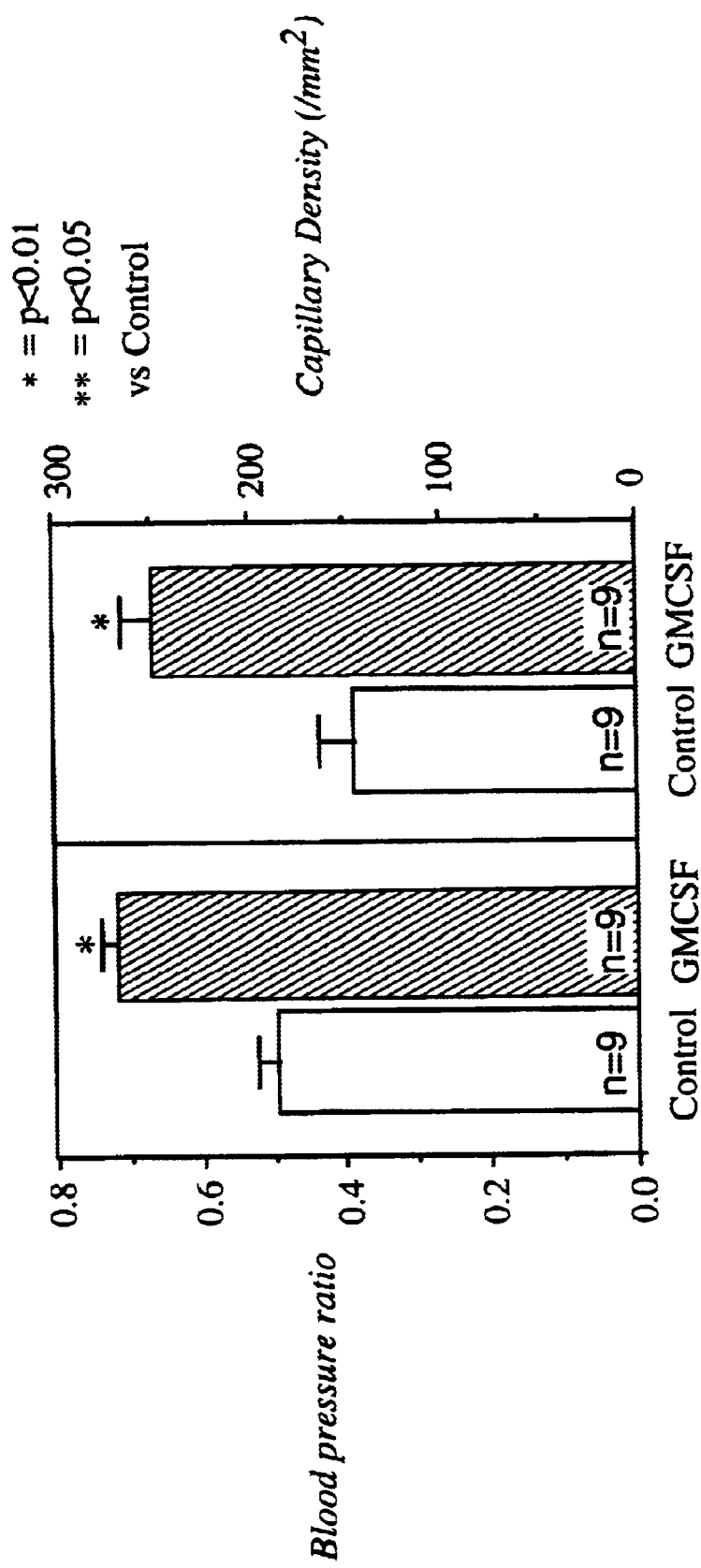

Cytokine-induced EPC Mobilization Enhances Neovascularization of Ischemic Tissues To determine if cytokine-induced EPC mobilization could enhance neovascularization of ischemic tissues, we employed the rabbit hindlimb ischemia model (Takeshita, et al., *J. Clin. Invest.* 1994;93:662–670). In GM-CSF pretreated rabbits (subcutaneous [s.c.] rhGM-CSF; 50 µg/day s.c.), EPC-enriched cell population was increased (189% compared to control animals), and EPC differentiation was enhanced (421% compared to control) at day 0 of (i.e., prior to) surgery (FIG. 3). Morphometric analysis of capillary density disclosed extensive neovascularization induced by GM-CSF pre-treatment compared to control (ischemia, no GM-CSF) group (249 vs 146/mm$^2$, p<0.01). GM-CSF pre-treatment also markedly improved ischemic limb/normal limb blood pressure ratio (0.71 vs 0.49, p<0.01) (FIGS. 3A–3C).

EXAMPLE 3

EPC Kinetics During Tissue Ischemia

To investigate EPC kinetics during tissue ischemia, the frequency and differentiation of EPCs were assessed by EPC isolation from peripheral blood and EPC culture assay. EPC-enriched fractions were isolated from mice as Sca-1 antigen-positive (Sca-1$^+$) cells, and from rabbits as the cell population depleted of T-lymphocytes, B-lymphocytes and monocytes (TBM$^-$), denoted by the antigen repertoire CD5-/Igµ-/CD11b-.

Figure 4A:
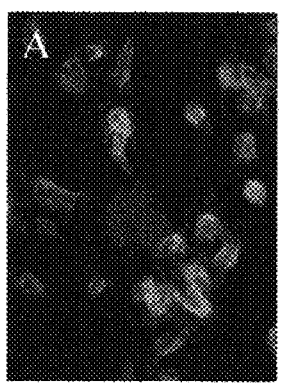

The frequency of EPC-enriched population marked by Sca-1 in the circulation was 10.7±1.0% in C57/6JBL normal mice. A subset of Sca-1$^+$ cells plated on rat vitronectin attached and became spindle-shaped within 5 days. Co-cultures of Sca-1$^+$ and Sca-1 negative (Sca-1$^-$) cells were examined after marking Sca-1$^+$ cells with DiI fluorescence. Sca-1$^+$ cells developed a spindle-shaped morphology. Mouse adherent cells in co-culture were found to be principally derived from DiI-marked Sca-1$^+$ cells (65~84%) and showed evidence of EC lineage by reaction with BS-1 lectin and uptake of acLDL[1] (FIG. 4A). To determine if Sca-1$^+$ cells can differentiate into ECs in vivo, a homogeneous population of DiI-marked Sca-1$^+$ cells, isolated from peripheral blood of the same genetic background, was administered intravenously to mice with hindlimb ischemia (Couffinhal, T., et al. *Am.J.Pathol.* (1998) day after ischemic surgery. DiI-labeled EPC-derived cells were shown to be differentiated in situ into ECs by co-staining for CD31 (PECAM) and were found incorporated into colonies, sprouts, and capillaries (FIGS. 4A–4D).

For the rabbit model, mature HCs were depleted using antibodies to T and B lymphocytes and monocytes, yielding an EPC-enriched (TBM$^-$) fraction. The frequency of TBM$^-$ EPC-enriched population in rabbit peripheral blood was 22.0±1.4%. Differentiation of EPCs was assayed by counting adherent cultured mononuclear blood cells. Adherent cells in EPC culture were found again to be derived principally from DiI-marked TBM$^-$ cells (7192%) and showed evidence of EC lineage by positive reaction with BS-1 lectin and uptake of acLDL.

Figure 4B:
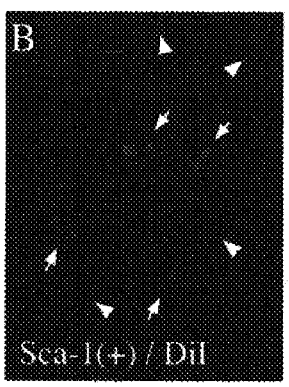
Figure 4C:
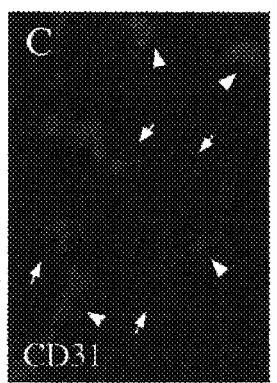
Figure 4D:
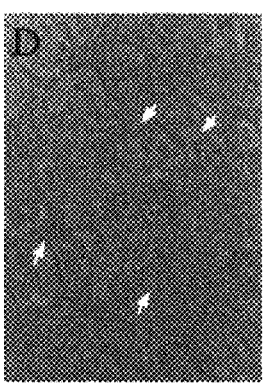

TBM cells were shown to differentiate into ECs in vivo by administration of autologous DiI-marked TBM$^-$ cells, isolated from 40 ml peripheral blood, to rabbits with unilateral hindlimb ischemia (Takeshita, S., et al. *J.Clin.Invest.* (1994) at 0, 3 and 7 days post-operatively. DiI-labeled EPC-derived cells differentiated in situ into ECs, shown by co-staining for CD31 and incorporation into colonies, sprouts, and capillaries (FIGS. 4E–4J). FIGS. 4A–4D are more particularly explained as follows. The figures provide fluorescent microscopic evidence that EPCs derived from isolated populations of Sca-1$^+$ cells in mice, and TBM$^-$ cells in rabbit, can home and incorporate into foci of neovascularization. In particular, in FIG. 4A cultured murine cells are shown, double-stained for acLDL-DiI (red) and BS-1 lectin (green) 4 days after EPC culture assay. (FIGS. 4B–D) Sca-1$^+$ cells administered to mouse with hindlimb ischemia have homed, differentiated and incorporated into foci of neovascularization in mouse ischemic hindlimb muscles 2 wks after surgery. FIGS. 4B and 4C document that DiI-labelled Sca-1$^+$ derived cells (red) co-localize with CD31 (green) indicdating that these EPCs have incorporated into CD31-positive vascularture. Arrows indicate cells positive for DiI and CD31 (derived from delivered EPCs), while arrowheads indicate CD31-positive, DiI-negative (autologous ECs). Non-fluorescent, phase contrast photograph in FIG. 1d documents vascular foci of EPCs (arrows) are within interstitial sites adjacent to skeletal myocytes.

FIGS. 4E–G show immunostaining of rabbit ischemic hindlimb muscle 2 wks after ischemia surgery shows accumulation and colonization of EPCs, in this case isolated as TBM$^-$ cells (red) (FIG. 4E); these cells were marked with DiI and reinjected at day 0, 3 and 7. FIG. 4F shows that these cells co-label with CD31, within neovascular foci. DAPI stains cell nuclei (blue) (FIG. 1G). (FIGS. 4H–J). Colonized TBM$^-$ cells are incorporated into developing sprouts, establishing new capillaries among skeletal myocytes.

EXAMPLE 4

Confirmation of EPC Kinetics During Tissue Ischemia

Figure 5C:
FIGS. 5C–F are representations of photomicrographs showing results of the mouse cornea micropocket assay with hindlimb ischemia. (5C–D) slit-lamp biomicroscopy, (5E–F) demonstration of neovascularization.
Figure 5D:
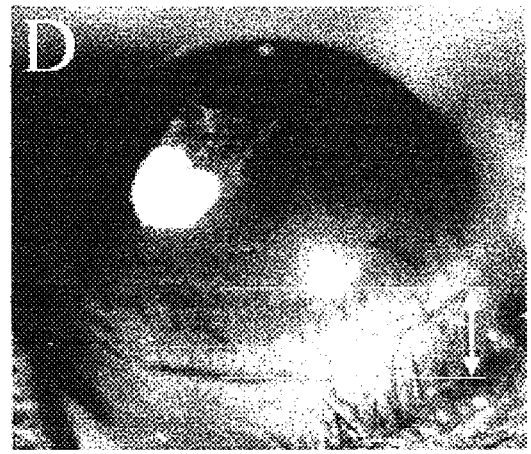
Figure 5E:
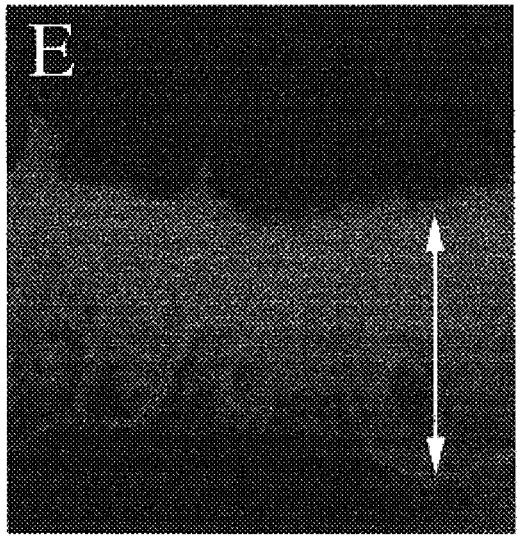
Figure 5F:
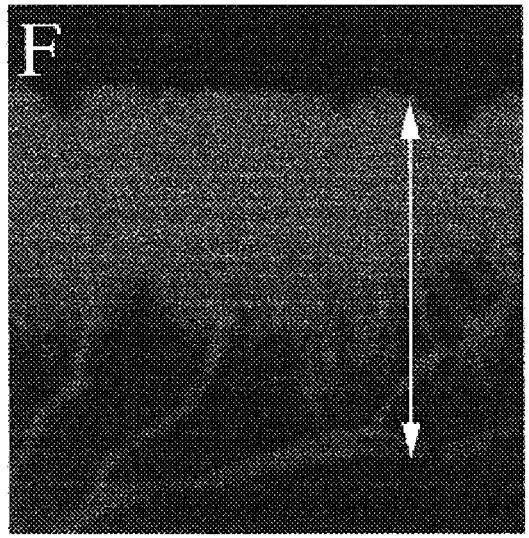
Figure 6A:
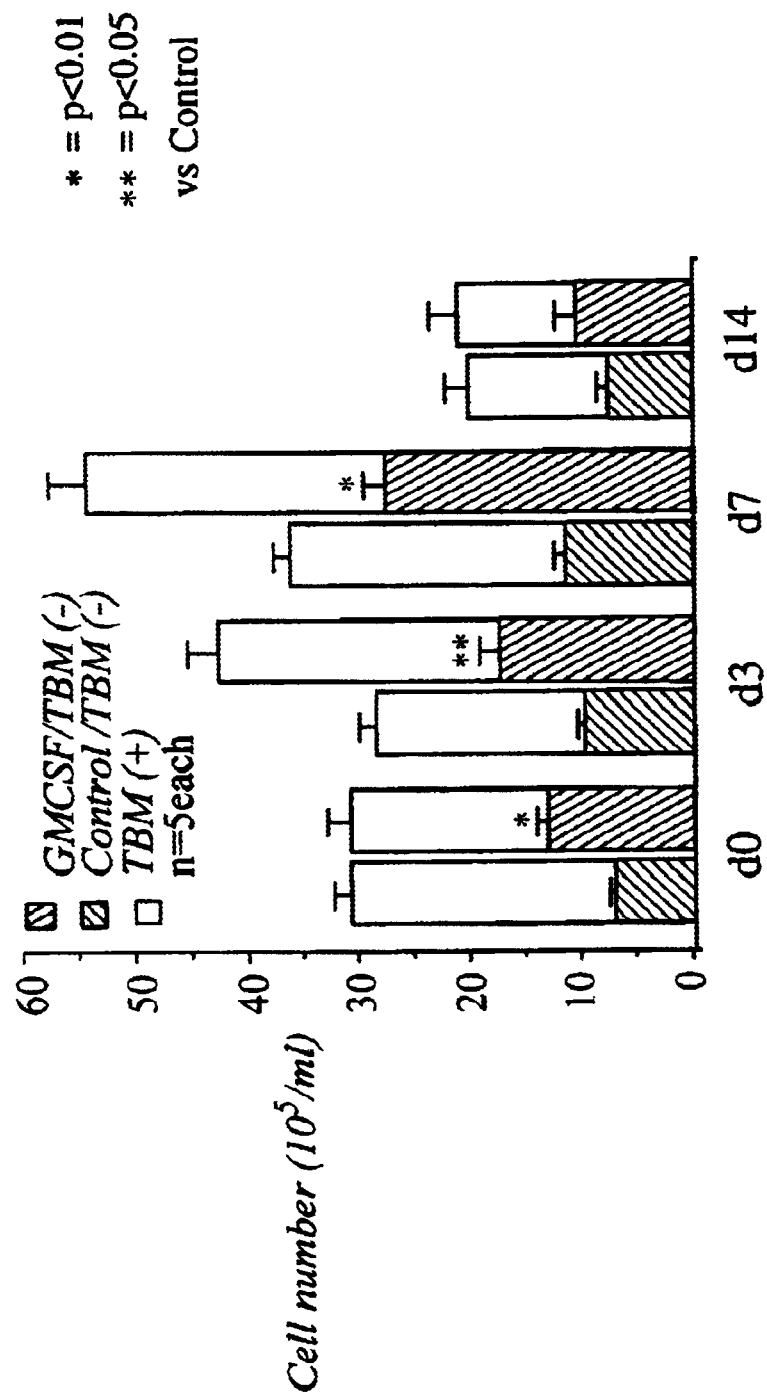
FIGS. 6A–C are graphs showing effect of GM-CSF-induced EPC mobilization on neovascularization in the rabbit ischemic hindlimb model.
Figure 6B:
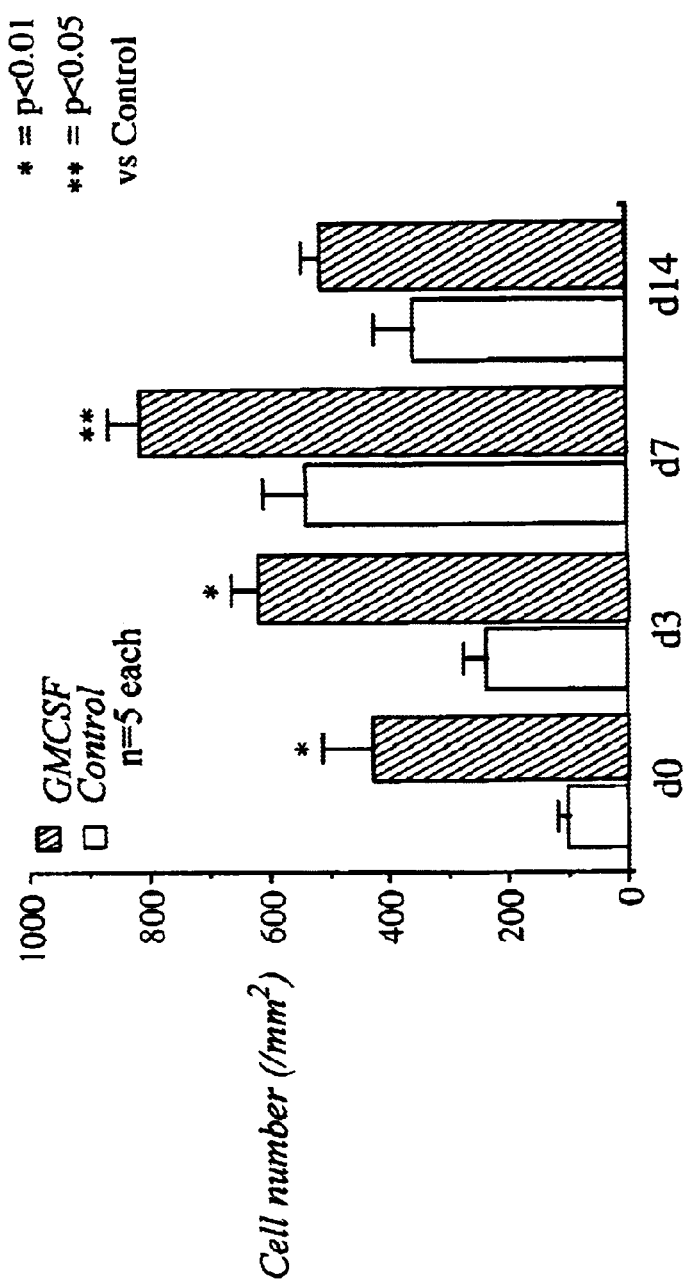

EPC kinetics during severe tissue ischemia were assayed for frequency and differentiation. The EPC-enriched population in circulating blood increased following the onset of ischemia, peaking at day 7 post-operatively (day 7 vs day 0: 17.5±2.4 vs 3.8±0.6×10$^5$/ml in mouse [p<0.05], 11.4±0.6 vs 6.7±0.3 10$^5$/ml in rabbit [p<0.05]) (FIGS. 5A, 6A). EPC assay culture demonstrated dramatic enhancement of EPC differentiation after ischemia, peaking at day 7 (day 7 vs day 0: 263±39 vs 67±14 /mm$^2$ in mouse [p<0.05], 539±73 vs 100±19 in rabbit [p<0.05]) (FIGS. 5B, 6B). Neither the frequency of the EPC-enriched population nor the EPC culture assay showed a significant increase in EPC kinetics in either sham-operated animal model at 7 days following surgery.

FIGS. 5A and 5B are more specifically explained as follows. The figures show EPC kinetics in relation to development of hindlimb ischemia. (FIG. 5A) Following surgery to create ischemic hindlimb, frequency of mouse EPC-enriched population (Sca-1$^+$) in circulating blood increases, becoming maximum by day 7 (n=5 mice at each time point). (FIG. 5B) Adherent cells in EPC culture are derived principally from DiI-marked Sca-1$^+$ cells. Assay culture demonstrates enhanced EPC differentiation after surgically induced ischemia with a peak at day 7 (n=5 each time point).

FIGS. 5C–H show results of the mouse cornea micropocket assay as applied to mice with hindlimb ischemia 7 days after surgery. Slit-lamp biomicroscopy (FIGS. 5C and 5D) and fluorescent photomicrographs (FIGS. 5E and 5F) demonstrate that neovascularization in avascular area of mouse cornea is enhanced by EPC mobilization induced by ischemia, shown with the same magnification. (FIGS. 5G and 5H) Quantitative analysis of two parameters, vessel length and circumferential distribution of neovascularization, indicates that corneal neovascularization was more profound in animals with hindlimb ischemia (n=7 mice) than in non-ischemic, sham control mice (n=9) (*=p<0.05).

EXAMPLE 5

Analysis of Impact of Enhanced EPC Mobilization on Neovascularization

Figures 5G, 5H:
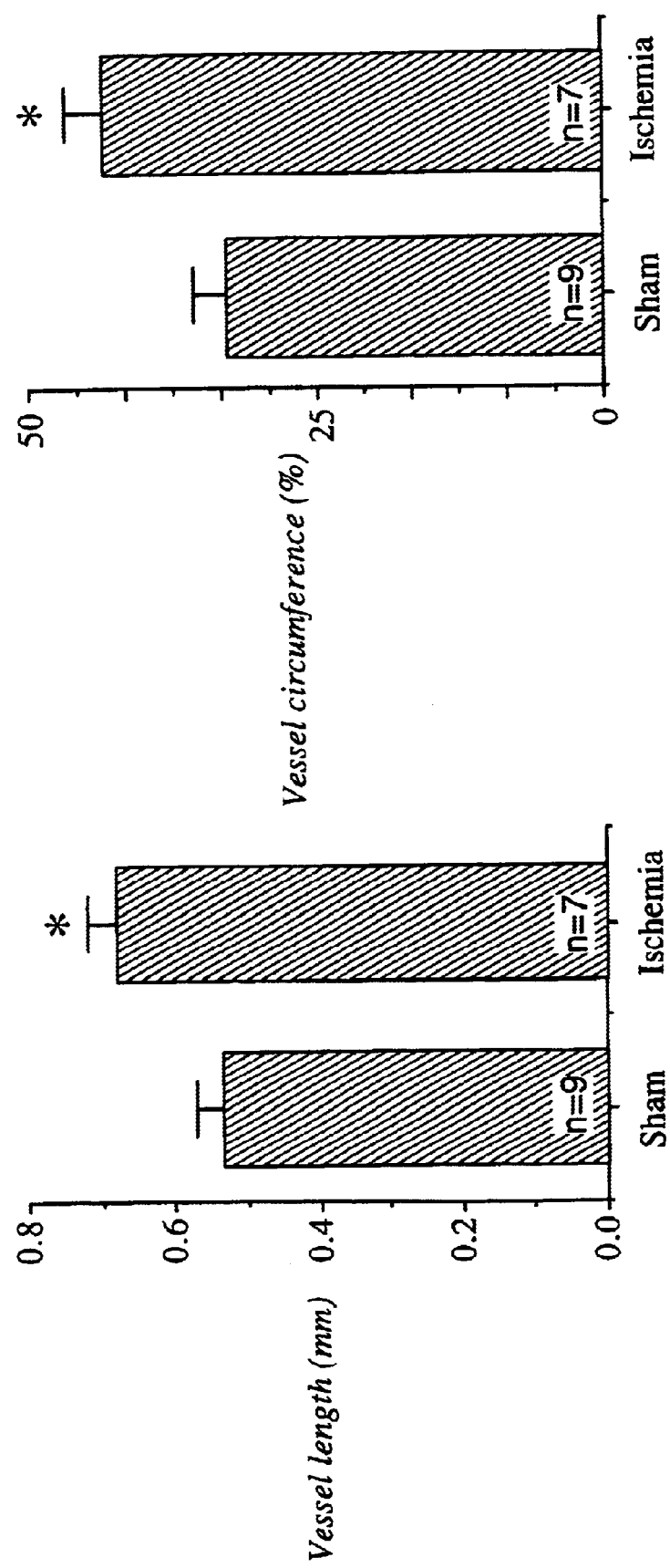
FIGS. 5G–H are graphs illustrating quantitation of vessel length and circumferential distribution of neovascularization.

To investigate the impact on neovascularization of enhanced EPC mobilization induced by ischemia, the mouse cornea micropocket assay was applied to animals in which hindlimb ischemia had been surgically created 3 days earlier. Slit-lamp (FIGS. 5C and 6D) and fluorescent (FIGS. 5E, 6F) photomicrographs documented that neovascularization of avascular mouse cornea was enhanced in animals with hindlimb ischemia compared to non-ischemic sham-operated controls. Measurements of vessel length and circumference showed a significant effect of EPC mobilization on neovascularization in ischemic animals versus sham control mice (length 0.67±0.04 vs 0.53±0.04 mm, p<0.05; circumference=43.3±3.5 vs 32.4±3.4%, p<0.05) (FIGS. 5G, 5H).

EXAMPLE 6

Figure 6C:
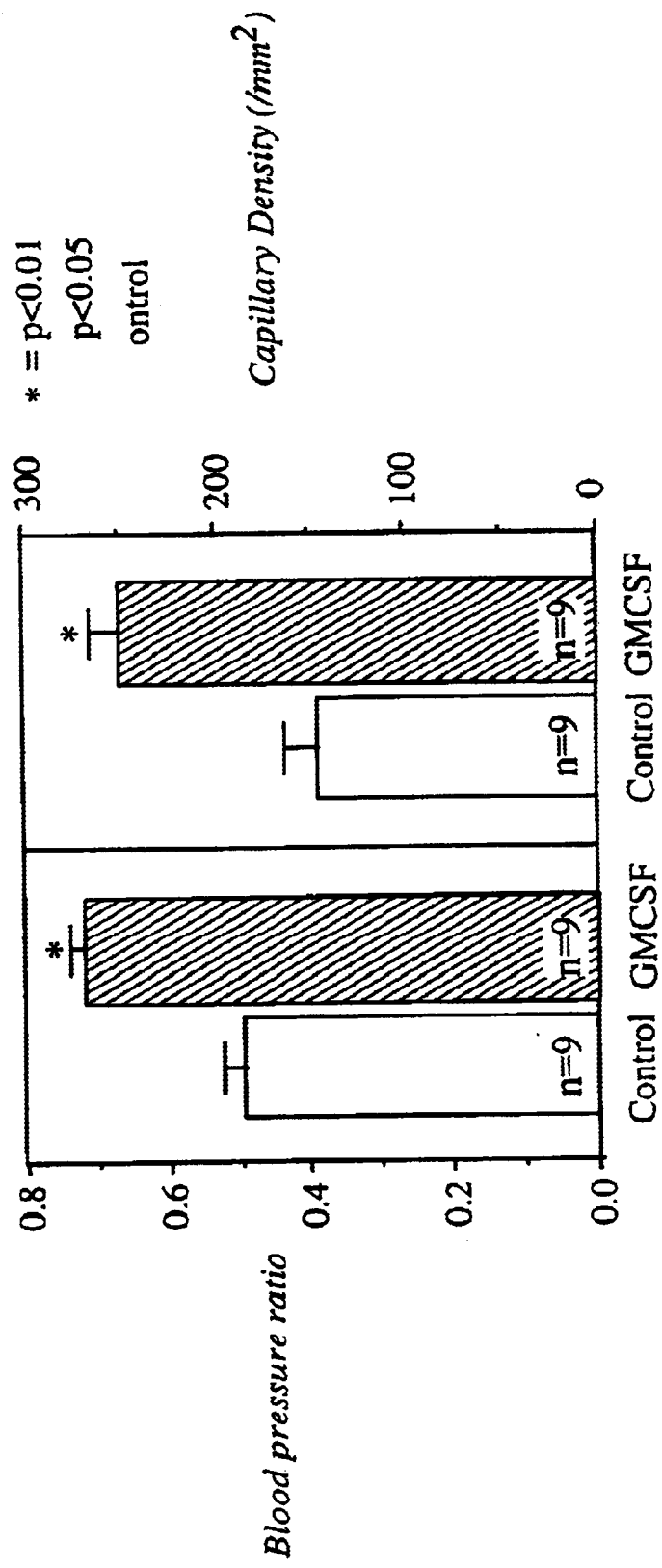
Figures 6D, 6E:
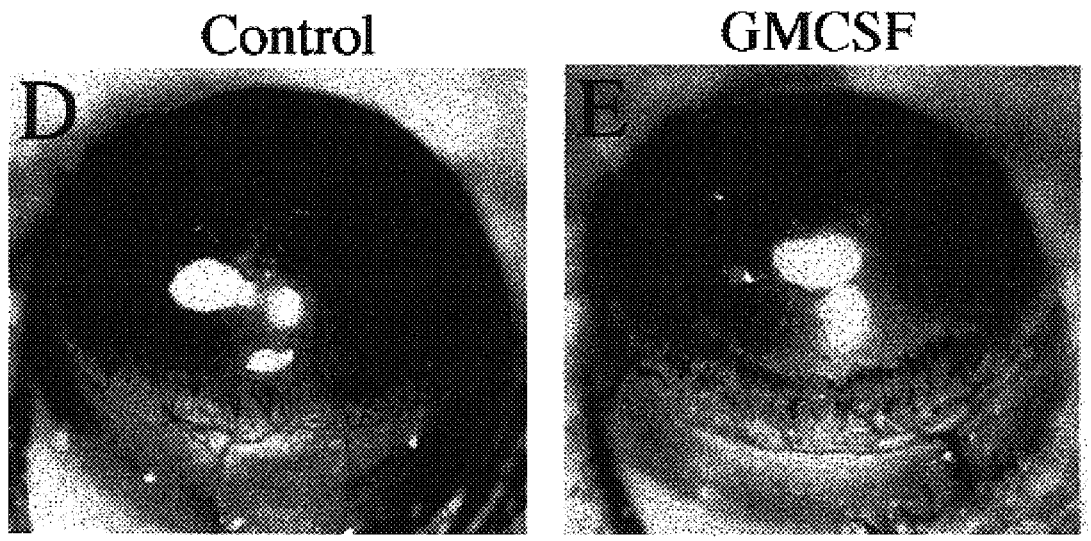
FIGS. 6D–G are representations of photomicrographs showing the GM-CSF induced effects described in FIGS. 6A–C. (6D, E) slit-lamp biomicroscopy, (6F, G) fluorescent photomicrographs.
Figures 6F, 6G:
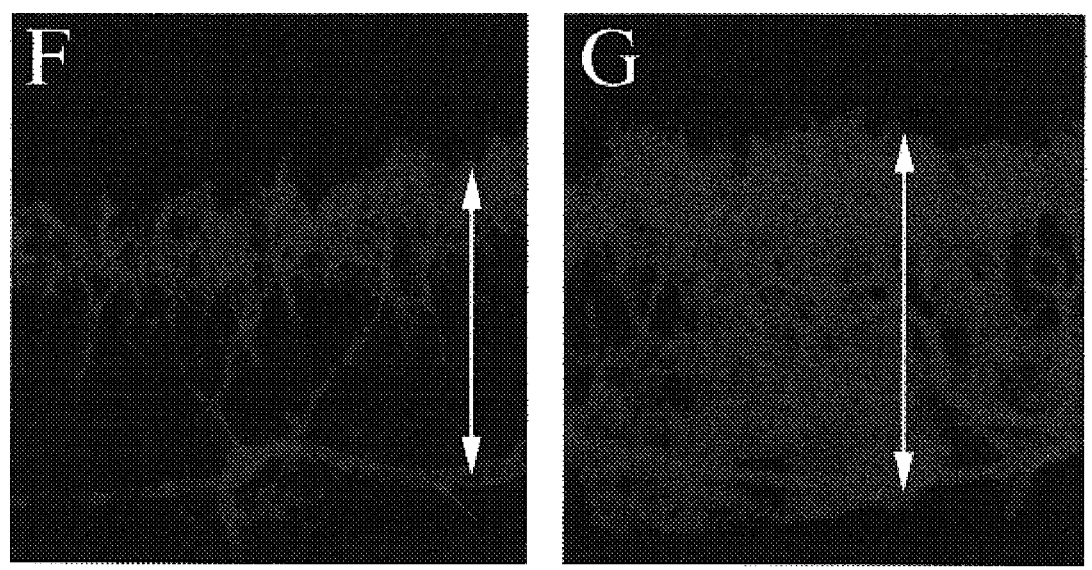
Figure 6I:
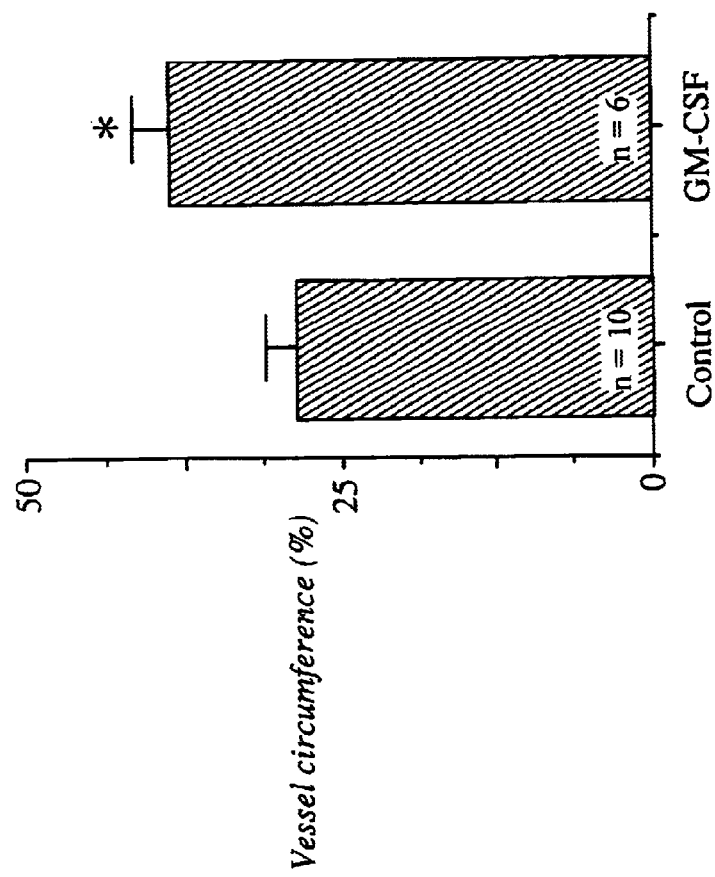
FIGS. 6H and 6I are graphs showing measurements of vessel length (6H) and vessel circumference (6I) taken from the experiment shown in FIGS. 6D–G.
Figure 6H:
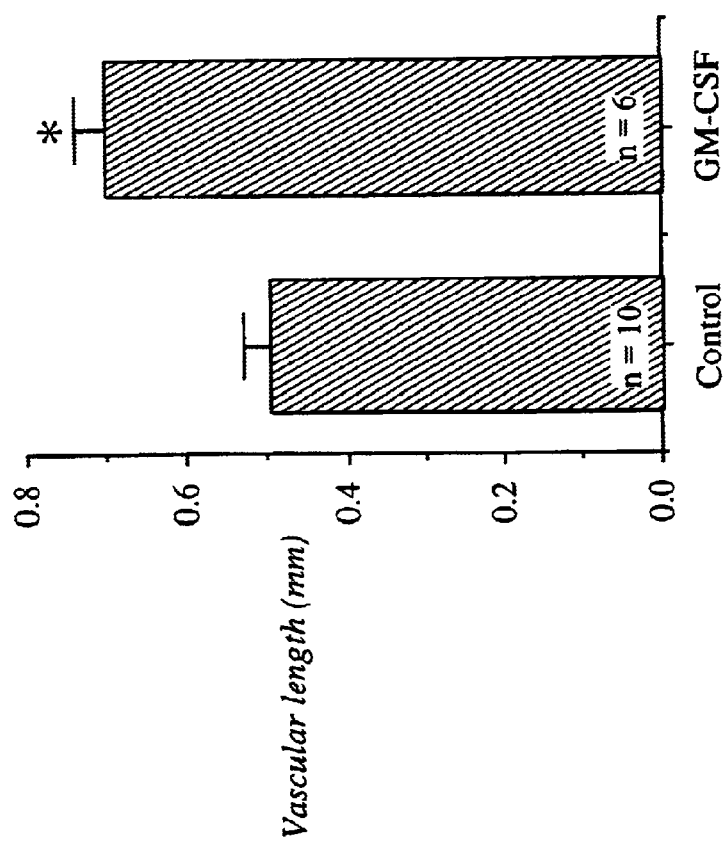

Confirmation of Enhanced Neovascularization With Cytokine-induced EPC Mobilization The rabbit model of hindlimb ischemia (Takeshita, S., et al. *J.Clin.Invest*. (1994)) was employed to determine if cytokine-induced EPC mobilization could enhance neovascularization of ischemic tissues. To effect GM-CSF-induced EPC mobilization while avoiding a direct effect on ECs, recombinant human GM-CSF was administered daily for 7 days prior to to development of hindlimb ischemia. Such GM-CSF pre-treatment (50 μg/day s.c.) increased the EPC-enriched population (12.5±0.8 vs 6.7±0.3×10$^5$/ml, p<0.01) and enhanced EPC differentiation (423±90 vs 100±19 /mm$^2$, p<0.01) at day 0 (day 7 of pre-treatment prior to surgery). By post-operative day 7, the frequency of circulating EPCs and EPC differentiation in GM-CSF-pretreated group exceeded control values (20.9±1.0 vs 11.3±2.5×10$^5$/ml [p<0.05], 813±54 vs 539±73 /mm$^2$ [p<0.01]) respectively (FIGS. 6A, 6B). Capillary density analysis documented extensive neovascularization induced by GM-CSF pre-treatment (249±18 vs 146±18 /mm$^2$ in untreated controls, p<0.01), as well as improved ischemic/normal hindlimb blood pressure ratio (0.71±0.03 vs 0.49±0.03, P<0.01) (FIG. 6C).

FIGS. 6A–I are explained in more detail as follows. The figures show the effect of GM-CSF-induced EPC mobilization on neovascularization in rabbit ischemic hindlimb model. (FIGS. 6A, B) Following pre-treatment with GM-CSF, circulating EPC-enriched population (TBM is increased in number compared to control (ischemic, untreated) animals beginning at day 0 (prior to surgery) through day 7 (FIG. 6A), as is EPC differentiation in culture (FIG. 5B) (n=5 mice at each time point). (FIG. 6C) Two weeks after onset of rabbit ischemia, physiological assessment using blood pressure ratio of ischemic to healthy limb indicates significant improvement in rabbits receiving GM-CSF versus control group. Moreover, histologic examination with alkaline phosphatase staining documented increased capillary density in GM-CSF treated rabbits compared to control group (n=9 mice in each group). (*=p<0.01, **=p<0.05).

Slit-lamp biomicroscopy (FIGS. 6D and 6E) and fluorescent photomicrographs (FIGS. 6F and 6G, same magnification) show that neovascularization in avascular area of mouse cornea is also enhanced by EPC mobilization induced by GM-CSF pretreatment. (FIGS. 6H and 6I) Measurements of vessel length and circumference indicate significant effect of EPC mobilization on neovascularization in GM-CSF pretreated (n=6) versus control mice (n=10) (*=p<0.05).

EXAMPLE 7

Confirmation of Enhanced Neovascularization Using the Mouse Cornea Micropocket Assay These results described above were corroborated by assessment of de novo vascularization in the mouse cornea micropocket assay. GM-CSF-pretreated mice (rmGM-CSF, 500 ng/day i.p.) developed more extensive corneal neovascularization than control mice (length=0.65±0.05 vs 0.53±0.04, p<0.05 mm; circumference=38.0±3.5 vs 28.3±2.7%, p<0.05) (FIGS. 6D–6I).

EXAMPLE 8

Enhanced BM-derived EPC Incorporation in the BM Transplantation Model

A murine BM transplantation (BMT) model was employed to establish direct evidence of enhanced BM-derived EPC incorporation into foci of corneal neovascularization in response to ischemia and GM-CSF. Corneas excised 6 days after micropocket implantation and examined by light microscopy demonstrated a statistically significant increase in cells expressing beta-galactosidase in the ischemic limb versus sham group (3.5±0.6 vs 10.5±1.7, p<0.01); the same was true for BMT recipients treated with GM-CSF vs control (3.2±0.3 vs 12.4±1.7, p<0.01) (FIGS. 7A, 7B). Corneas from control mice (post-BMT) disclosed no cells expressing β-galactosidase. Quantitative chemical detection confirmed a statistically significant increase in β-galactosidase activity among mice receiving GM-CSF vs controls (2.90±0.30 vs 2.11±0.09×10$^3$, p<0.05) (FIG. 7C).

Figure 7A:
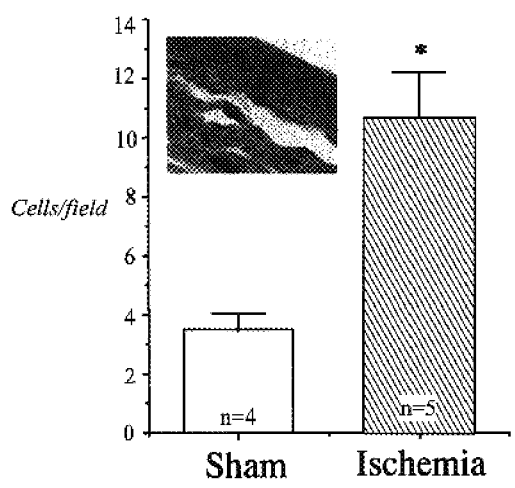
Figure 7B:
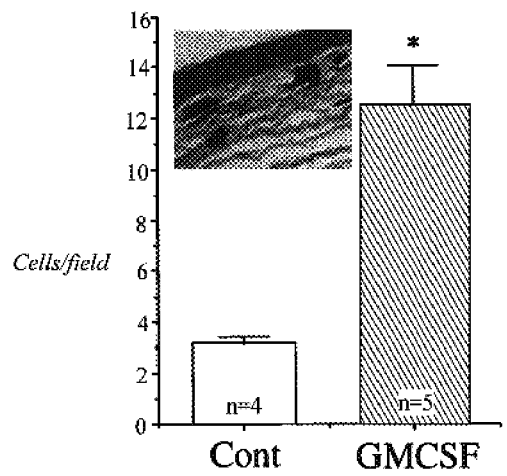

FIGS. 7A–C are explained in more detail as follows. The figures illustrate that Bone marrow-derived EPCs contribute to corneal neovascularization. Photomicrographs shown as inserts document incorporation of BM-derived EPCs expressing endothelial-specific Tie-2/lacZ (blue cells) into foci of corneal neovascularization, both in mice with hindlimb ischemia (FIG. 7A), as well as in rabbits pretreated with GM-CSF (FIG. 7B). The frequency of incorporated EPCs stained by X-gal was manually counted under light microscopy. (FIG. 7A) Incorporated EPCs were significantly more frequent in mice with hindlimb ischemia vs the sham-operated mice; (FIG. 7B) the same was true for rabbits receiving GM-CSF group vs control rabbits (*=p<0.01 for each condition). (FIG. 7C) β-galalactosidase activity was significantly higher in GM-CSF group than control group **=p<0.05).

The development of limb ischemia was observed to induce EPC mobilization, and these EPCs consequently contribute to "vasculogenic" neovascularization. Ledney et al (Ledney, G. D., et al *J.Surg.Res*. (1985) reported that wound trauma causes mobilization of HCs including pluripotent stem or progenitor cells in spleen, BM, and peripheral blood. Because EPCs are derived from BM and EPC mobilization is enhanced during tissue ischemia, circulating EPCs may constitute a reparative response to ischemic injury, controlled by BM via circulating cytokines and soluble receptors and/or adhesive molecules.

The results indicate that GM-CSF exerts a potent stimulatory effect on EPC kinetics and that such cytokine-induced EPC mobilization can enhance neovascularization of severely ischemic tissues as well as de novo vascularization of previously avascular sites. In particular, the Examples show mobilization of EPCs in response to endogenous and exogenous stimuli.

The discussion and Examples above addressed the significance of We investigated the endogenous stimuli, namely tissue ischemia, and exogenous cytokine therapy, specifically granulocyte macrophage-colony stimulating factor (GM-CSF), in the mobilization of EPCs and induction of neovascularization of ischemic tissues. Development of regional ischemia in both mice and rabbits was found to increase the frequency of circulating EPCs. In mice, the impact of ischemia-induced EPC mobilization was shown by enhanced ocular neovascularization following cornea micropocket surgery in animals with hindlimb ischemia compared to non-ischemic controls. In rabbits with hindlimb ischemia, circulating EPCs were further augmented following GM-CSF pre-treatment, with a corresponding improvement in hindlimb neovascularization. Direct evidence that EPCs which contributed to enhanced corneal neovascularization were specifically mobilized from the bone marrow (BM) in response to ischemia and GM-CSF was documented in mice transplanted with BM from transgenic donors expressing □-galacotsidase transcriptionally regulated by the endothelial cell (EC) specific Tie-2 promoter. These findings indicate that circulating EPCs are mobilized endogenously in response to tissue ischemia or exogenously by cytokine therapy and thereby augment neovascularization of ischemic tissues.

In particular, the concept of EPC mobilization and subsequent neovascularization as disclosed herein and in the co-pending U.S. Provisional Application No. 60/077,262 is believed to represent a potent strategy for the prevention and treatment of a variety of ischemic vascular diseases including those specifically mentioned herein.

General Comments- The following Materials and Methods were used as needed in the Examples above.

1. Isolation of Mouse EPC-enriched Fraction From Peripheral Blood

Peripheral blood samples of mice were obtained from the heart immediately before sacrifice, and separated by Histopaque-1083 (Sigma, St. Louis, Mo.) density gradient centrifugation at 400 g for 20 min. The light-density mononuclear cells were harvested, washed twice with Dulbecco's phosphate buffered saline supplemented with 2 mM EDTA (DPBS-E) and counted manually. Blood mononuclear cells in each animal were suspended in 500 µl of DPBS-E buffer supplemented with 0.5% bovine serum albumin (Sigma) with 50 µl of Sca-1 microbeads (Miltenyi Biotec, Auburn, Calif.) for 15 min at 4° C. After washing cells with buffer, Sca-1 antigen positive (Sca-1$^+$) cells were separated with a magnetic stainless steel wool column (Miltenyi Biotec) and counted. Cells which did not bind to antibodies for Sca-1 passed through the column, while Sca-1$^+$ cells were retained. The Sca-1$^+$ cells were eluted from the column and both cell fractions were counted manually.

Isolation of Rabbit EPC-enriched Fraction From Peripheral Blood

Rabbit peripheral blood samples were obtained from either ear vein through a 20G infusion catheter and separated by Histopaque-1077 (Sigma) density gradient centrifugation at 400 g for 20 min. The light-density mononuclear cells were harvested, washed twice by DPBS-E and counted manually. As an appropriate antibody for rabbit hematopoietic stem/precursor cells is not available, immatureHCs were isolated by depletion of matureHCs. The cells were incubated with mixed primary antibodies (Serotec) of mouse anti-rabbit CD5, anti-rabbit IgM ($\mu$ chain) and CD11b to recognize mature T and B lymphocytes and monocytes respectively. After washing antibodies, the cells were incubated with secondary rat anti-mouse IgG microbeads (Miltenyi Biotec) and placed in a magnetic separation column (Miltenyi Biotec). Cells which did not bind to antibodies for mature T and B lymphocytes and monocytes (TBM$^-$), identical to hematopoietic stem/precursor cells, passed through the column, while cells positive for cocktail antibodies were retained. The positive cells (TBM$^+$), matureHCs, were eluted from the column and both cell fractions were counted manually.

3. EPC Differentiation Assay

To evaluate EPC differentiation from circulating blood cells, Sca-1$^+$ and Sca-1$^-$ cells isolated from 700 µl peripheral blood of each mouse, as well as TBM$^-$ and TBM$^+$ cells isolated from 2 ml peripheral blood of each rabbit, were co-cultured in one well of a 24-well plate coated with rat plasma vitronectin (Sigma) after DiI-labeling of Sca-1$^+$ or TBM$^-$ cells in EBM-II media supplemented with 5% FBS (Clonetics, San Diego, Calif.). After four days in culture, cells were washed twice with media, and attached spreading cells were counted according to the frequency of DiI-labeled Sca-1$^+$ or TBM$^-$ cell-derived cells and non-labeled Sca-1$^-$ or TBM$^+$ cell-derived cells.

To determine the cell type of attached spindle shaped cells in the above assay, identical cells were assayed by acLDL-DiI uptake and BS-1 lectin reactivity. Double-positive cells were judged as EPCs and counted (96.2±1.8% in mouse and 95.5±2.4% in rabbit).

4. Study Design for Evaluation of Circulating EPC Kinetics Following Ischemia

C57 BL/6J mice (n=40) with hindlimb ischemia were sacrificed at days 0 (before surgery), 3, 7 and 14 postoperatively (10 mice at each timepoint). Sham-operated mice were sacrificed at day 7 post-operatively as well (n=4). Peripheral blood mononuclear cells were prepared for counting of Sca-1$^+$ cells, as an EPC-enriched fraction, by magnetic bead selection (n=5) and EPC culture assay (n=5).

In New Zealand White rabbits (n=24) with hindlimb ischemia, peripheral blood mononuclear cells were isolated at post-operative days 0, 3, 7 and 14 in order to prepare for counting of TBM$^-$ cells by magnetic bead selection and EPC culture assay. Sham-operated rabbits were examined at day 7 postoperatively as well (n=4).

To evaluate the effect of ischemia-induced circulating EPCs on neovascularization, a corneal neovascularization assay (Kenyon, B. M., et al. *Invest Ophthalmol Vis Sci* (1996) and Asahara, T. et al. *Circ.Res*. (1998) was performed in mice with hindlimb ischemia. Three days after ischemia or sham surgery, C57BL/6J mice (n=5 each) underwent corneal assay microsurgery, including measurement of neovasculature length and circumference 6 days after corneal surgery (9 days after ischemia). In situ BS-1 lectin staining was performed prior to sacrifice.

5. Study Design for GM-CSF Effect on Circulating EPC Kinetics and Neovascularization These experiments were intended to demonstrate the effect of GM-CSF on EPC kinetics and consequent vasculogenic contribution to neovascularization.

a. Rabbit model. Animals with hindlimb ischemia were divided into 2 groups. GM-CSF treatment, administered to 8 rabbits, consisted of recombinant human GM-CSF (70 μg/day) injected subcutaneously daily for one week, beginning 7 days before surgery (GM-CSF group). The ischemic control group consisted of 8 rabbits receiving subcutaneous injections of saline daily for one week before surgery (control group).

Rabbits were investigated on the day immediately before initial injection (day [−]7), the day of ischemic surgery (day 0), and 3, 7, 14 days postoperatively (days 3, 7, 14), at which time peripheral blood was isolated from the central ear artery. At each timepoint, 5 ml of blood was isolated for cell counting and culture assay. In all animals from each group, the blood pressure ratio between the ischemic and healthy limb was measured and on day 14 (at sacrifice), capillary density of ischemic muscles was determined as well (vide infra).

b. Mouse model Following recombinant murine GM-CSF (0.5 μg/day) or control saline by i.p. injection daily for one week, beginning at day [−]7 through day [−]1, C57BL/6J mice (n=5 each) underwent corneal micropocket surgery at day 0 and the length and circumference of the consequent neovasculature was measured at day 6. In situ BS-1 lectin staining was performed before sacrifice.

6. Murine Bone Marrow Transplantation Model

FVB/N mice underwent BMT from transgenic mice constitutively expressing □-galactosidase encoded by lacZ under the transcriptional regulation of an EC-specific promoter, Tie-2 (Schlaeger, T.m. et al. *Development* (1995). Reconstitution of the transplanted BM yielded Tie-2/LZ/BMT mice in which expression of lacZ is restricted to BM-derived cells expressing Tie-2; lacZ expression is not observed in other somatic cells. The Tie-2/LZ/BMT mice then underwent corneal assay microsurgery (Kenyon, B. M. et al. *Invest Ophthalmol Vis Sci* (1996) and (Asahara, T. et al. *Circ.Res.* (1998), 3 days following ischemia or sham operation, or 1 day following completion of a 7-day course of GM-CSF or control vehicle.

BM cells were obtained by flushing the tibias and femurs of age-matched (4 wk), donor Tie-2 transgenic mice (FVB/N-TgN[TIE2LacZ]182 Sato, Jackson Lab). Low-density BM mononuclear cells were isolated by density centrifugation over Histopaque-1083 (Sigma). BM transplantation (BMT) was performed in FVB/N mice (Jackson Lab) lethally irradiated with 12.0 Gy and intravenously infused with approximately $2 \times 10^6$ donor BM mononuclear cells each. At 4 wks post-BMT, by which time the BM of the recipient mice was reconstituted, the mice underwent surgery to create hindlimb ischemia (vide infra) or a sham operation; 3 days later, microsurgery for assay of corneal neovascularization was performed. Likewise, at 4 wks post-BMT, GM-CSF or control vehicle was administered for a period of 7 days; 1 day after completion of GM-CSF or control pre-treatment, surgery for cornea neovascularization assay was performed. Corneas of BMT animals were harvested at 6 days after corneal microsurgery for light microscopic evidence of β-galactosidase expression or chemical detection of β-galactosidase activity.

7. Detection of β-Galactosidase Expression in Corneal Tissue

For histological detction of β-galactosidase-expressing cells, the whole eye of the mouse was enucleated, fixed in 4% paraformaldehyde for 2 hours at 4° C., and incubated in X-gal solution overnight at 37° C. The sample was then placed in PBS and the hemisphered cornea was excised under the dissecting microscope and embedded for histologic processing. Histologic samples were counterstained with light hematoxylin-and-eosin and examined by light microscopy to manually count the number of X-gal positive cells per cross-section. Three sections were examined from each tissue sample and averaged for evaluation of X-gal stained cell frequency.

For chemical detection of β-galactosidase activity, the enucleated eye was placed into liquid nitrogen, and stored at −80° C. The assay was performed using Chemiluminescence Reporter Gene Assay System, Galacto-Light Plus TM (Tropix Inc., Bedford Mass.) according to the modified protocol.

Briefly, the eye was placed in 1 ml of supplemented lysis buffer, and after adding 0.5 mM DTT was homogenized with a Tissuemizer Mark II (Tekmar Co., Cincinatti, Ohio). Homogenized lysis solution was centrifuged to remove debris. An aliquot of the supernatant from homogenized lysis buffer was used for protein measurement using a BCA Protein Assay kit (PIERCE, Rockford, Ind.). The supernatant was assayed after treatment with ion exchange resin, Chelex 100, and beta-galactosidase activity was measured using a chemiluminometer (Lumat LB9501, Berthold, Nashua, N.H.). beta-galactosidase activity was standardized according to protein concentration.

8. Mouse Model of Hindlimb Ischemia

We used age-mached (8 wks) C57BL/6J male mice (Jackson Lab, Bar Harbor, Me.) to create a mouse model of hindlimb ischemia (Couffinhal, T. et al. *Am.J.Pathol* (1998). All animals were anesthetized by intraperitoneal (i.p.) pentobarbital injection (160 mg/kg) for subsequent surgical procedures. A skin incision was performed at the middle portion of the left hindlimb overlying the femoral artery. The femoral artery then was gently isolated and the proximal portion of the femoral artery was ligated with a 3-0 silk ligature. The distal portion of the saphenous artery was ligated, and other arterial branches as well as veins were all dissected free, then excised. The overlying skin was closed using two surgical staples. After surgery, mice were kept on a heating plate at 37° C, and special care was taken to monitor the animals until they had completely recovered from anesthesia.

9. Rabbit Model of Hindlimb Ischemia

We used a rabbit ischemic hindlimb model described previously (Takeshita, S. et al. *J.Clin.Invest.* (1994). A total of 20 New Zealand White rabbits (3.8–4.2 kg) (Pine Acre Rabbitry, Norton, Mass.) were anesthetized with a mixture of ketamine (50 mg/kg) and acepromazine (0.8 mg/kg) following premedication with xylazine (2 mg/kg). A longitudinal incision was then performed, extending inferiorly from the inguinal ligament to a point just proximal to the patella. The limb in which the incision was performed was determined randomly at the time of surgery by the operator. Through this incision, using surgical loupes, the femoral artery was dissected free along it entire length; all branches of the femoral artery, including the inferior epigastric, deep femoral, lateral circumflex, and superficial epigastric, were also dissected free. After dissecting the popliteal and saphenous arteries distally, the external iliac artery and all of the above arteries were ligated with 4.0 silk (Ethicon, Sommerville, N.J.). Finally, the femoral artery was completely excised from its proximal origin as a branch of the external iliac artery, to the point distally where it bifurcates to form the saphenous and popliteal arteries. Following excision of the femoral artery, retrograde propagation of thrombus leads to occlusion of the external iliac artery. Blood flow to the ischemic limb consequently becomes dependent upon collateral vessels issuing from the internal iliac artery.

10. Mouse Corneal Neovascularization Assay

Age-mached (8 wk) C57BL/6J male mice (Jackson Lab) were used to evaluate mouse corneal neovascularization. All animals were anesthetized by i.p. pentobarbital injection (160 mg/kg) for subsequent surgical procedures. Corneal micropockets were created with a modified von Graefe cataract knife in the eyes of each mouse. Into each pocket, a 0.34×0.34 mm sucrose aluminum sulfate (Bukh Meditec, Denmark) pellet coated with hydron polymer type NCC (IFN Science, New Brunswick, N.J.) containing 150 ng of vascular endothelial growth factor (VEGF) was implanted. The pellets were positioned 1.0 mm from the corneal limbus and erythromycin ophthalmic ointment (E. Foufera, Melville, N.Y.) was applied to each operated eye. The corneas of all mice were routinely examined by slit-lamp biomicroscopy on postoperative days 5 through 6 after pellet implantation. Vessel length and circumference of neovascularization were measured on the sixth postoperative day when all corneas were photographed. After these measurements, mice received 500 $\mu$g of Bandeiraea Simplicifolia lectin-1 (BS- 1) conjugated with FITC (Vector Lab, Burlingame, Calif.), an EC-specific marker, intravenously, and were then sacrificed 30 minutes later. The eyes were enucleated and fixed in 1% paraformaldehyde solution. After fixation, the corneas were placed on glass slides and studied by fluorescent microscopy.

11. Lower Limb Blood Pressure Ratio

These in vivo physiologic studies were performed on anesthetized rabbits. Blood pressure was measured in both hindlimbs. On each occasion, the hindlimbs were shaved and cleaned, the pulse of the posterior tibial artery was identified with a Doppler probe, and the systolic blood pressure in each limb was measured using standard techniques. The blood pressure ratio was defined for each rabbit as the ratio of systolic pressure of the ischemic limb to the systolic pressure of the normal limb.

12. Capillary Density

The extent of neovascularization was assessed by measuring the frequency of capillaries in light microscopic sections taken from the normal and ischemic hindlimbs. Tissue specimens were obtained as transverse sections from muscles of both limbs of each animal at the time of sacrifice. Muscle samples were embedded in O.C.T. compound (Miles, Elkhart, Ind.) and snap-frozen in liquid nitrogen. Multiple frozen sections 5 $\mu$m in thickness were then cut from each specimen so that the muscle fibers were oriented in a transverse fashion. The tissue sections were stained for alkaline phosphatase with an indoxyl-tetrazolium method to detect capillary ECs as previously described and counterstained with eosin. Capillaries were counted under a 20×objective to determine the capillary density (mean number of capillaries/mm$^2$). Ten different fields were randomly selected for the capillary counts. The counting scheme used to compute the capillary/muscle fiber ratio was otherwise identical to that used to compute capillary density. See Prokop, D. J. (1997) *Science*, 276: 71; Perkins, S and Fleischman, R. A. (1988) *J. Clinical Invest.* 81: 1072; Perkins, S and Fleischman, R. A. (1990) *Blood* 75: 620.

13. Statistical Analysis

All results are expressed as mean +standard error (m±SE). Statistical significance was evaluated using unpaired Student's t test for comparisons between two means. The multiple-comparison between more than 3 groups was performed with the use of ANOVA. A value of p<0.05 was interpreted to denote statistical significance.

The following references are specifically incorporated herein by reference:

(1) Asahara, T., Murohara, T., Sullivan, A., et al. Isolation of putative progenitor endothelial cells for angiogenesis. *Science* 275,965–967 (1997).

(2) Folkman, J. & Klagsbrun, M. Angiogenic factors. *Science* 235,442–447 (1987).

(3) Soldi, R., Primo, L., Brizzi, M. F., et al. Activation of JAK2 in human vascular endothelial cells by granulocyte-macrophage colony-stimulating factor. *Blood* 89,863–872 (1997).

(4) Bussolino, F., Wang, J. M., Turrini, F., et al. Stimulation of the Na+/H+ exchanger in human endothelial cells activated by granulocyte- and granulocyte-macrophage-colony stimulating factor. Evidence for a role in proliferation and migration. *J.Biol.Chem.* 264, 188284–18287 (1989).

(5) Aglietta, M., Piacibello, W., Sanavio, F., et al. Kinetics of human hematopoietic cells after in vivo adminstration of granulocyte-macrophage colony-stimulating factor. *J.Clin.Invest.* 83,551–557 (1989).

(6) Fleischman, R., Simpson, A. F., Gallardo, T., Jin, X. L. & Perkins, S. Isolation of endothelial-like stromal cells that express Kit ligand and support in vitro hematopoiesis. *Exp Hematol* 23,1407–1416 (1995).

(7) Flanagan, M. F., Fujii, A. M., Colan, S. D., Flanagan, R. G. & Lock, J. E. Myocardial angiogenesis and coronary perfusion in left ventricular pressure-overload hypertrophy in the young lamb: evidence for inhibition with chronic protamine administration. *Circ.Res.* 68,1458–1470 (1991).

(8) Takahashi, T. et al. (1998) Ischemia-and cytokine-induced mobilization of bone marrow-derived endothelial progenitor cells for neovasularization. *Nature Medicine* 5: 1–7.

What is claimed is:

1. A method for inducing formation of new blood vessels in ischemic tissue of a mammal, wherein the method comprises:

a) isolating endothelial progenitor cells (EPCs) from the mammal, the EPCs comprising at least one of the following markers: CD34$^+$, flk-1$^+$ and tie-2$^+$, b) contacting the isolated EPCs with an amount of an angiogenic protein sufficient to induce proliferation of the EPCs; and c) administering to the mammal the proliferated EPCs in an amount sufficient to induce the formation of the new blood vessels in the mammal, wherein the method further comprises administering to the ischemic tissue of the mammal granulocyte-macrophage colony-stimulating factor (GM-CSF) or an effective fragment thereof.

2. The method of claim 1, wherein the mammal comprises injured blood vessels.

3. The method of claim 2, wherein the invasive manipulation is balloon angioplasty, or deployment of a stent or catheter.

4. The method of claim 3, wherein the stent is an endovascular stent.

5. The method of claim 1 further comprising co-administering at least one angiogenic protein.

6. The method of claim 1 further comprising co-administering to the ischemic tissue at least one angiogenic protein.

7. The method of claim 6, wherein the angiogenic protein is an endothelial cell mitogen.

8. The method of claim 7, wherein the angiogenic protein is acidic fibroblast growth factor (aFGF), basic fibroblast growth factor (bFGF), vascular endothelial growth factor (VEGF-1), epidermal growth factor (EGF), transforming growth factor α and β (TGF-α and TFG-β), platelet-derived endothelial growth factor (PD-ECGF), platelet-derived growth factor (PDGF), tumor necrosis factor α (TNF-α), hepatocyte growth factor (HGF), insulin like growth factor (IGF), erythropoietin, colony stimulating factor (CSF), macrophage CSF (M-CSF), angiopoetin-1 (Ang1) or nitric oxide synthetase (NOS); or an effective fragment thereof.

9. The method of claim 8, wherein the protein is one of VEGF-B, VEGF-C, VEGF-2, VEGF-3; or an effective fragment thereof.

10. A pharmaceutical product for inducing neovascularization in a mammal, wherein the product comprises isolated endothelial progenitor cells (EPCs) and is formulated to be physiologically acceptable to a mammal, the product being sterile and further comprising at least one angiogenic protein, wherein the product further comprises granulocyte-macrophage colony-stimulating factor (GM-CSF).

11. A kit for inducing formation of new blood vessels in ischemic tissue of a mammal, wherein the kit comprises the isolated progenitor cells (EPCs) and optionally at least one angiogenic protein, the kit further optionally comprising a pharmacologically acceptable carrier solution, wherein the kit further comprises granulocyte-macrophage colony-stimulating factor (GM-CSF).

12. The kit of claim 11, wherein the kit further comprises a stent, catheter or syringe for delivering the EPCs.

13. The method of claim 1 further comprising co-administering directly to the ischemic tissue a nucleic acid encoding an endothelial cell mitogen.

14. A method for inducing formation of new blood vessels in ischemic tissue of a mammal, wherein the method comprises:
   a) isolating endothelial progenitor cells (EPCs) from the mammal, the EPCs comprising at least one of the following markers: $CD34^+$, $flk-1^+$ and $tie-2^+$,
   b) contacting the isolated EPCs with an amount of an angiogenic protein sufficient to induce proliferation of the EPCs; and
   c) administering to the mammal the proliferated EPCs in an amount sufficient to induce the formation of the new blood vessels in the mammal, wherein the angiogenic protein is granulocyte-macrophage colony-stimulating factor (GM-CSF) or an effective fragment thereof.

15. The method of claim 14, wherein the method further comprises administering to the ischemic tissue of the mammal granulocyte-macrophage colony-stimulating factor (GM-CSF) or an effective fragment thereof.

16. The method of claim 14 further comprising co-administering directly to the ischemic tissue a nucleic acid encoding an endothelial cell mitogen.

17. The method of claim 1 or 14 further comprising co-administering to the ischemic tissue of the mammal at least one hematopoietic factor.

18. The method of claim 17, wherein the hematopoietic factor is granulocyte-colony stimulating factor (G-CSF).

19. A method for inducing formation of new blood vessels in ischemic tissue of a mammal, wherein the method comprises:
   a) isolating endothelial progenitor cells (EPCs) from the mammal, the EPCs comprising at least one of the following markers: $CD34^+$, $flk-1^+$ and $tie-2^+$,
   b) contacting the isolated EPCs with an amount of a hematopoietic factor sufficient to induce proliferation of the EPCs; and
   c) administering to the mammal the proliferated EPCs in an amount sufficient to induce the formation of the new blood vessels in the mammal, wherein the hematopoietic factor is a colony stimulating factor (CSF).

20. The method of claim 19, wherein the colony stimulating factor (CSF) is granulocyte-colony stimulating factor (G-CSF).

21. The method of claim 19 further comprising co-administering to the ischemic tissue of the mammal at least one hematopoietic factor.

22. The method of claim 21, wherein the hematopoietic factor is a colony stimulating factor (CSF).

23. The method of claim 22, wherein the colony stimulating factor (CSF) is granulocyte-colony stimulating factor (G-CSF).

24. The method of claim 19 further comprising co-administering directly to the ischemic tissue a nucleic acid encoding an endothelial cell mitogen.

* * * * *